US009456974B2

(12) United States Patent
Krueger et al.

(10) Patent No.: US 9,456,974 B2
(45) Date of Patent: *Oct. 4, 2016

(54) HAIR CARE COMPOSITIONS WITH SELECTED PROTEIN HYDROLYSATES AND SELECTED COMPLEXES OF ACIDIC PROTEIN HYDROLYSATES AND BASIC FATTY ACID AMIDOAMINES

(71) Applicant: Henkel AG & Co. KGaA, Duesseldorf (DE)

(72) Inventors: Marcus Krueger, Ellerhoop (DE); Jorg Kahre, Leichlingen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/614,546

(22) Filed: Feb. 5, 2015

(65) Prior Publication Data

US 2015/0150772 A1 Jun. 4, 2015

Related U.S. Application Data

(63) Continuation of application No. PCT/EP2013/064215, filed on Jul. 5, 2013.

(30) Foreign Application Priority Data

Aug. 9, 2012 (DE) ........................ 10 2012 214 139

(51) Int. Cl.
  *A61Q 5/12* (2006.01)
  *A61K 8/64* (2006.01)
  *A61K 8/42* (2006.01)
  *A61Q 5/00* (2006.01)

(52) U.S. Cl.
  CPC . *A61K 8/64* (2013.01); *A61K 8/42* (2013.01); *A61Q 5/002* (2013.01); *A61Q 5/12* (2013.01)

(58) Field of Classification Search
  None
  See application file for complete search history.

(56) References Cited

U.S. PATENT DOCUMENTS

| 5,034,219 A | 7/1991 | Deshpande et al. |
| 5,188,756 A | 2/1993 | Baker et al. |
| 2009/0041709 A1* | 2/2009 | Hoffmann ............... A61K 8/731 424/70.12 |
| 2009/0169644 A1* | 7/2009 | Goddinger ............. A61K 8/922 424/642 |
| 2009/0304620 A1* | 12/2009 | Schulze zur Wiesche ................. A61K 8/84 424/70.12 |
| 2010/0028272 A1* | 2/2010 | Knappe ................. A61K 8/8152 424/47 |
| 2011/0033407 A1* | 2/2011 | Krueger .................... A61K 8/97 424/70.9 |
| 2012/0288463 A1 | 11/2012 | Yoshioka et al. |

OTHER PUBLICATIONS

Vegetamide 18 MEA product brochure (Mar. 2011).*
PCT International Search Report (PCT/EP2013/064215) dated Oct. 15, 2014.
Database GNPD [Online] Mintel, "Enhance Nourishing Conditioner", XP002731129, Database accession No. 10227299, Aug. 2005.
Database GNPD [Online] Mintel, "Styling Gel", XP002727937, Database accession No. 569844, Aug. 2006.
Database GNPD [Online] Mintel, "Volumising Shampoo", XP002731113, Database accession No. 587137, Sep. 2006.
Database GNPD [Online] Mintel, "Curl Energizing Shampoo", XP002731128, Database accession No. 752184, Aug. 2007.
Database GNPD [Online] Mintel, "Hair Body Building Shampoo", XP002731112, Database accession No. 1425006, Nov. 2010.
Database GNPD [Online] Mintel, "Shaping Mousse", XP002731111, Database accession No. 1439264, Dec. 2010.
Database GNPD [Online] Mintel, "Shampoo", XP002731127, Database accession No. 1649420, Oct. 2011.
Kobayashi, "Hair Conditioning Ingredients Developed with Focusing on Hair Surface Structure", XP002727880, SOFW-Journal, vol. 138, pp. 28-36, 2012.

* cited by examiner

*Primary Examiner* — Jyothsna Venkat
(74) *Attorney, Agent, or Firm* — David K. Benson

(57) ABSTRACT

Hair treatment agents include selected protein hydrolysates and selected complexes of acidic protein hydrolysates and basic fatty acid amidoamines.

8 Claims, No Drawings

HAIR CARE COMPOSITIONS WITH SELECTED PROTEIN HYDROLYSATES AND SELECTED COMPLEXES OF ACIDIC PROTEIN HYDROLYSATES AND BASIC FATTY ACID AMIDOAMINES

FIELD OF THE INVENTION

The present invention generally relates to hair treatment agents including selected protein hydrolysates and selected complexes of acidic protein hydrolysates and basic fatty acid amidoamines.

BACKGROUND OF THE INVENTION

There is a requirement to bring about further improvement in hair care products and to provide them with further advantageous properties. In particular, there is a need to provide a conditioning complex which can ideally also be used in conjunction with oxidizing agents and surfactant agents.

Environmental influences and oxidative hair treatments often lead to impaired combability of both dry and wet hair. Furthermore, gloss and moisture balance are deleteriously affected by the attacked external structure of the keratinic fibers. A further consequence of repeated treatment of keratinic fibers with surfactant and/or oxidative agents is for severe greasiness to return to the keratinic fibers and for there to be a strong tendency towards increased dandruff formation.

It is therefore desirable to reduce the side-effects of environmental influences and of oxidative and surfactant hair treatments preferably not only as early as during the oxidative or surfactant hair treatment but also after the oxidative or surfactant hair treatment without impairing the effectiveness of the oxidative or surfactant cosmetic preparation, in particular with regard to color intensity, color fastness, lightening performance or permanent-wave action, and of preventing the keratinic fibers from becoming greasy again and increased dandruff formation. Furthermore, it is also desirable, in the case of a 2-in-1 product, to combine in one application step the oxidative treatment of keratin-containing fibers, in particular human hair, with the application of effective fiber protection from environmental influences, for example UV protection.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has now surprisingly been found that the above-mentioned objectives are solved excellently by a hair treatment agent which includes an active substance complex including as essential ingredients at least one selected protein hydrolysate and at least one selected complexes of an acidic protein hydrolysate and a basic fatty acid amidoamine.

Hair treatment agents including this active substance complex lead to an improvement in softening, an improvement in gloss, an improvement in moisture balance and to protection from oxidative damage and to the prevention of the keratinic fibers becoming greasy again and to an increase in the washing resistance of dyed keratinic fibers, in particular human hair and to a delay in the formation of dandruff.

A cosmetic composition including in a suitable cosmetic carrier, in each case relative to the total weight of the composition, at least one protein hydrolysate in a total quantity of 0.01 to 10.0 wt. %, and at least one selected complex of an acidic protein hydrolysate and a basic fatty acid amidoamine in a total quantity of 0.01 to 10.0 wt. %.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention firstly provides a hair treatment agent including in a suitable cosmetic carrier, in each case relative to the total composition of the agent
a) at least one selected protein hydrolysate in a total quantity of 0.01 to 10.0 wt. %,
b) at least one selected complex of an acidic protein hydrolysate and a basic fatty acid amidoamine in a total quantity of 0.01 to 10.0 wt. %.

Using this combination results in surprisingly good properties of the treated hair, in particular in improved combability, improved gloss and improved elasticity and in distinctly increased washing resistance of dyed hair, and in extended durability simultaneously combined with better shaping performance in waving processes such as wet set and permanent wave.

Hair treatment agents for the purposes of the present invention are for example shampoos, hair conditioners, conditioning shampoos, hair conditioners, hair masks, hair packs, hair tonics, hair coloring shampoos or combinations thereof. In particular, hair treatment agents according to the invention are taken to be hair conditioning compositions such as hair conditioners, hair masks, hair packs, hair oils and lotions both as leave-on products, i.e. products which remain on the hair until the next hair wash, and as rinse-off products, i.e. products to be rinsed out again a few seconds to a few hours after application.

Combability is taken according to the invention to mean both combability of the wet fibers and combability of the dry fibers.

Handle is defined as the tactile properties of a fiber assembly, wherein a person skilled in the art feels and carries out a sensory evaluation of the body and silkiness of the assembly.

Shaping is taken to mean the ability to impart a change in shape to an assembly of previously treated keratin-containing fibers, in particular human hair. In relation to hair cosmetics, it is also known as stylability.

Restructuring for the purposes of the invention is understood to mean reducing the damage to keratinic fibers arising as a result of the widest possible range of influences. A significant role is played here, for example, by the restoration of natural strength. Restructured fibers are distinguished by improved gloss, by improved handle and by easier combability. In addition, they display optimized strength and elasticity. Successful restructuring may furthermore be detected physically as an increase in melting point in comparison with the damaged fiber. The higher the melting point of the hair, the stronger the structure of the fibers.

Washing fastness for the purposes of the invention is taken mean retention of the original coloring with regard to shade and/or intensity when the keratinic fibers are exposed repeatedly to the influence of aqueous agents, in particular surfactant-containing agents such as shampoos.

The compositions according to the invention including the active substance complex according to the invention are furthermore distinguished by a distinctly improved state of the keratinic fibers with regard to the moisture balance of the keratinic fibers. The active substance complex according to the invention furthermore results in clear protection of the keratinic fibers from the effects of heat, for example when blow-drying keratinic fibers. Protecting the surface of keratinic fibers from the effect of heat is in particular of great significance when using hair straighteners or hairdryers. Finally, it has surprisingly been found that the compositions according to the invention result in distinctly delayed resoiling of the keratinic fibers.

An aqueous cosmetic carrier includes at least 50 wt. % water.

For the purposes of the present invention, aqueous-alcoholic cosmetic carriers should be taken to be aqueous solutions including 3 to 70 wt. % of a $C_1$-$C_6$ alcohol, in particular methanol, ethanol or propanol, isopropanol, butanol, isobutanol, tert.-butanol, n-pentanol, iso-pentanols, n-hexanol, iso-hexanols, glycol, glycerol, 1,2-pentanediol, 1,5-pentanediol, 1,2-hexanediol or 1,6-hexanediol. The agents according to the invention may additionally include further organic solvents, such as for example methoxybutanol, benzyl alcohol, ethyl diglycol or 1,2-propylene glycol. Any water-soluble organic solvents are here preferred. Water is more preferred.

The first ingredient a) according to the invention is a protein hydrolysate. According to the invention, protein hydrolysates are degradation products of proteins which are produced by an acidic, basic or enzymatic reaction. As a result of the production process, protein hydrolysates exhibit a molecular weight distribution. Protein hydrolysates according to the invention also include oligopeptides since the latter may likewise be produced by corresponding reactions from proteins. Individual amino acids which assume the form of discrete individual compounds are not included among protein hydrolysates for the purposes of the present invention. Furthermore, the protein hydrolysates according to the invention differ from the protein hydrolysates which are a component of the ionic complex prepared from an acidic protein hydrolysate and a basic fatty acid amidoamine.

Protein hydrolysates of both plant and animal origin or marine or synthetic origin may be used according to the invention.

Animal protein hydrolysates are for example elastin, collagen, keratin, silk and milk protein hydrolysates which may also assume salt form. Such products are distributed for example under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), ProSina® (Croda) and Kerasol® (Croda).

Further plant protein hydrolysates which are preferred according to the invention are for example soy, almond, pea, moringa, potato, and wheat protein hydrolysates. Such products are obtainable for example under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), Crotein® (Croda) and Puricare® LS 9658 from Laboratoires Sérobiologiques.

Further protein hydrolysates which are preferred according to the invention are of maritime origin. These include for example collagen hydrolysates from fish or seaweed and protein hydrolysates from mussels or pearl hydrolysates. Examples of pearl extracts according to the invention are the commercial products Pearl Protein Extract BG® or Crodarom® Pearl.

Protein hydrolysates and their derivatives furthermore include cationized protein hydrolysates, wherein the underlying protein hydrolysate may originate from animals, for example from collagen, milk or keratin, from plants, for example from wheat, maize, rice, potatoes, soy or almonds, from marine life forms, for example from fish collagen or algae, or biotechnologically obtained protein hydrolysates. Typical examples of the cationic protein hydrolysates and derivatives according to the invention which may be mentioned are those that are commercially obtainable and mentioned among the INCI names in the "International Cosmetic Ingredient Dictionary and Handbook", (seventh edition 1997, The Cosmetic, Toiletry, and Fragrance Association 1101 17th Street, N.W., Suite 300, Washington, D.C. 20036-4702).

Oligopeptides are likewise protein hydrolysates according to the invention. Oligopeptides may be preferred in the hair treatment agents according to the invention due to their defined amino acid sequence. An oligopeptide which comprises at least one amino acid sequence Glu-Glu-Glu

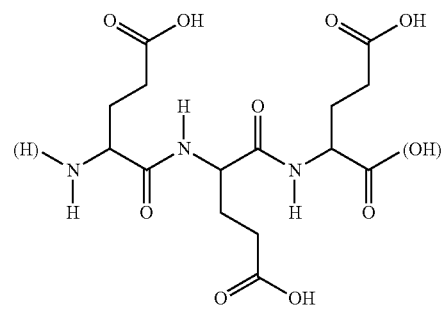

wherein the amino group may assume free or protonated form and the carboxy groups may assume free or deprotonated form may be more preferred according to the invention.

In this and in all the following formulae, the bracketed hydrogen atom of the amino group and likewise the bracketed hydroxyl group of the acid function mean that the groups in question may be present as such (in which case the compound is an oligopeptide with the relevant number of amino acids as shown in the formula above) or alternatively that the amino acid sequence is present in an oligopeptide which comprises still further amino acids—depending on where the further amino acid(s) is/are attached, the bracketed components of the above-stated formula are replaced by the further amino acid residue(s).

Oligopeptides for the purposes of the present application are amino acid condensation products linked by acid amide type peptide bonds and which include at least 3 and a maximum of 25 amino acids. In hair treatment agents which are preferred according to the invention, the oligopeptide comprises 5 to 15 amino acids, preferably 6 to 13 amino acids, more preferably 7 to 12 amino acids and in particular 8, 9 or 10 amino acids. Depending on whether further amino acids are attached to the Glu-Glu-Glu sequence and depending on the nature of these amino acids, the molar mass of the oligopeptides present in the agents according to the invention may vary. Hair treatment agents which are preferred according to the invention are characterized in that the oligopeptide has a molar mass of 650 to 3000 Da, preferably of 750 to 2500 Da, more preferably of 850 to 2000 Da and in particular of 1000 to 1600 Da. As is evident from the preferred number of amino acids in the oligopeptides and the preferred molar mass range, it is preferred to use oligopeptides which do not solely consist of the three glutamic acids, but instead comprise further amino acids attached to said sequence. These further amino acids are preferably selected from specific amino acids, while certain other representatives are less preferred according to the invention. A more preferred oligopeptide additionally includes tyrosine which is preferably attached via the acid function thereof to the Glu-Glu-Glu sequence. Hair treatment agents which are preferred according to the invention are therefore characterized in that the oligopeptide present therein comprises at least one amino acid sequence Tyr-Glu-Glu-Glu wherein the amino group may assume free or protonated form and the carboxy groups may assume free or deprotonated form.

A further more preferred oligopeptide additionally includes isoleucine which is preferably attached via the acid function thereof to the Glu-Glu-Glu sequence. Hair treatment agents which are preferred according to the invention are therefore characterized in that the oligopeptide present therein comprises at least one amino acid sequence Glu-Glu-Glu-Ile wherein the amino group may assume free or protonated form and the carboxy groups may assume free or deprotonated form.

Oligopeptides which comprise both of the above-stated amino acids (tyrosine and isoleucine) are preferred according to the invention. Greater preference is here given to hair treatment agents according to the invention in which the oligopeptide present therein comprises at least one amino acid sequence Tyr-Glu-Glu-Glu-Ile wherein the amino group may assume free or protonated form and the carboxy groups may assume free or deprotonated form.

Further preferred oligopeptides additionally include arginine, which is preferably attached to isoleucine.

Still more preferred oligopeptides additionally include valine, which is preferably attached to arginine. Hair treatment agents which are further preferred according to the invention are therefore characterized in that the oligopeptide present therein comprises at least one amino acid sequence Tyr-Glu-Glu-Glu-Ile-Arg-Val

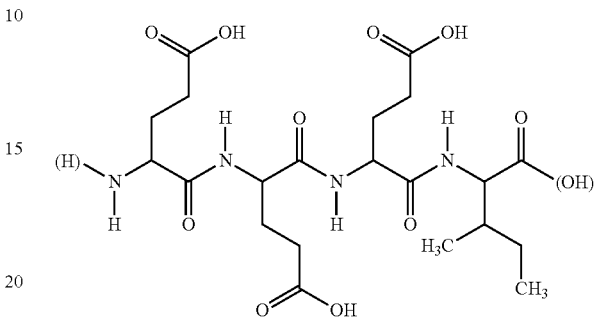

wherein the amino groups may assume free or protonated form and the carboxy groups may assume free or deprotonated form. Still more preferred oligopeptides additionally include leucine, which is preferably attached to valine. Hair treatment agents which are further preferred according to the invention are characterized in that the oligopeptide present therein comprises at least one amino acid sequence Tyr-Glu-Glu-Glu-Ile-Arg-Val-Leu compositions according to the invention. In the present application, the term amino acid is also taken to mean a structure which includes only one permanently cationic group per molecule, such as for example choline. This term is furthermore also taken to mean substances such as carnitine or taurine, since, like amino acids, they occur naturally in biological systems and in many cases behave like amino acids.

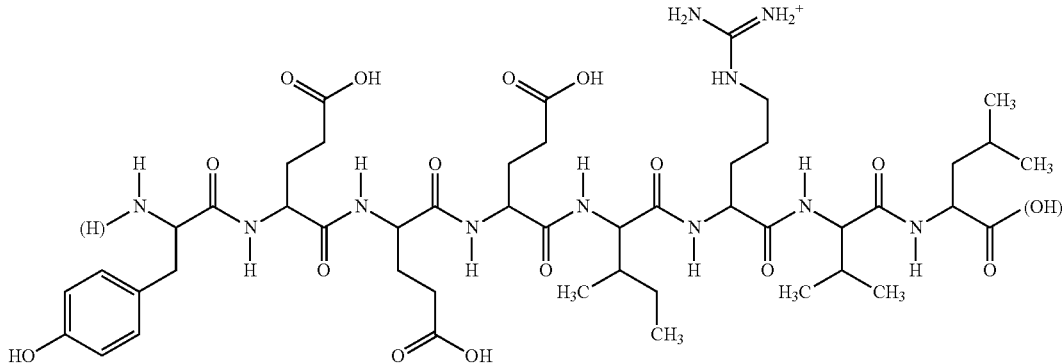

wherein the amino groups may assume free or protonated form and the carboxy groups may assume free or deprotonated form.

More preferred oligopeptides additionally include leucine, which is preferably attached to tyrosine. Hair treatment agents which are further preferred according to the invention are characterized in that the oligopeptide present therein comprises at least one amino acid sequence Leu-Tyr-Glu-Glu-Glu-Ile-Arg-Val-Leu Amino acids according to the invention are selected from alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, thyroxine, tryptophan, tyrosine, valine, betaine, ornithine, 1,1-dimethylproline, hercynine (N,N,N-trimethyl-L-histidine betaine), ergothioneine (thioneine, 2-mercapto-N,N,N-trimethyl-L-histidine betaine), carnitine, taurine and choline and mixtures thereof. All kinds of isomers, such as for example

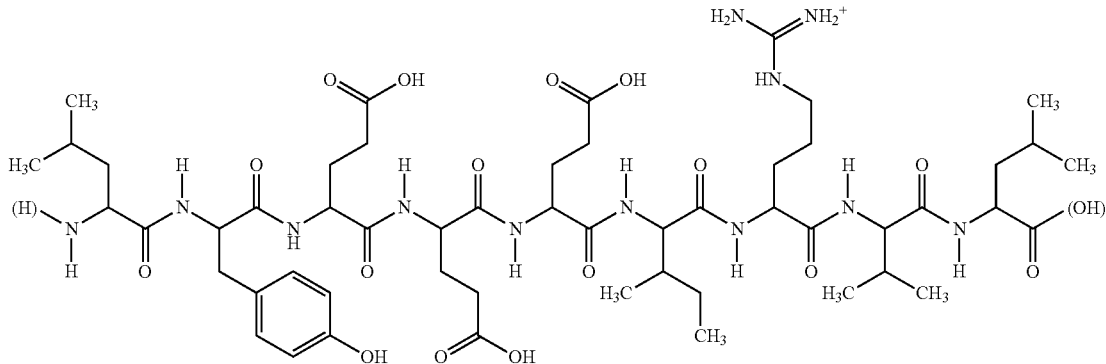

wherein the amino groups may assume free or protonated form and the carboxy groups may assume free or deprotonated form.

Protein hydrolysates which are more preferred according to the invention are for example based on keratin, silk, wheat, moringa and marine protein hydrolysates. Protein hydrolysates based on silk, keratin and wheat are highly preferred.

The protein hydrolysates are present in the compositions in concentrations of 0.001 wt. % to 20 wt. %, preferably of 0.05 wt. % to 15 wt. % and particularly preferably in quantities of 0.05 wt % to 5 wt. %.

In addition to the protein hydrolysates according to the invention, amino acids may furthermore be used in the diastereomers, enantiomers, cis-trans isomers, optical isomers, conformational isomers and racemates may be used according to the invention.

Alanine, arginine, asparagine, glutamic acid, glutamine, glycine, histidine, hydroxylysine, hydroxyproline, isoleucine, leucine, lysine, proline, serine, betaine, ornithine, 1,1-dimethylproline, carnitine, taurine, choline and mixtures thereof are more preferentially used. Arginine, glutamine, glycine, histidine, lysine, proline, serine, betaine, carnitine, taurine and mixtures thereof are particularly preferably used.

Arginine, glutamine, histidine, lysine, carnitine and taurine and mixtures thereof are highly preferably used.

Most highly preferably used are arginine, glutamine, carnitine and taurine as are mixtures of arginine and taurine,
glutamine and taurine,
glutamine and carnitine,
arginine and glutamine,
carnitine and taurine, and mixtures of
arginine, carnitine and taurine,
glutamine, carnitine and taurine.

The hair treatment agents according to the invention include the amino acids as previously described in a total quantity, relative to the total agent, of 0.01 to 10.0 wt. %, more preferably of 0.05 to 7.0 wt. %, particularly preferably of 0.1 to 5.0 wt. %. If mixtures of at least two amino acids are used, the same quantities as stated above apply. In the case of mixtures, the individual amino acids are used in a ratio of 5:1 to 1:5. The ratio is relative to the weight ratio of the amino acids. If a mixture of three amino acids is used, said amino acids are in each case used in identical proportions by weight.

The second mandatory component of the active substance complex is an ionic complex consisting of an acidic protein hydrolysate and a basic fatty acid amidoamine. In the present invention, an acidic protein hydrolysate is preferably taken to mean a plant protein hydrolysate. The protein hydrolysate moiety may, of course, also originate from any desired protein source. Plant protein hydrolysates such as soy, almond, pea, moringa, potato and wheat protein hydrolysates are preferred. Collagen hydrolysates from fish or seaweed and protein hydrolysates from mussels or pearl hydrolysates are likewise included according to the invention. The protein hydrolysate of the ionic complex according to the invention is in any event case a protein hydrolysate which differs from the protein hydrolysate of active ingredient component a) according to the invention. It is, however, essential for the present invention for the proportion of acidic amino acids in the hydrolysate to amount to at least 10 wt. %, preferably 20 wt. %, more preferably 30 wt. % and highly preferably 40 wt. %. Protein hydrolysates which meet this condition form the ionic complexes according to the invention of an acidic protein hydrolysate and a basic fatty acid amidoamine of the present invention. Protein hydrolysates based on elastin, collagen, keratin, silk and milk protein are also possible, although not preferred, according to the invention.

Possible fatty acid amidoamines are any fatty acid amidoamine with a chain length of 8 to 40 carbon atoms in the chain. The fatty acid amidoamines may here be saturated or unsaturated, straight-chain or branched. The fatty acid amidoamines according to the invention are preferably of the following structure:

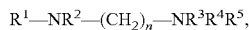

in which $R^1$ denotes a linear or branched, saturated or unsaturated acyl residue with 8 to 40 C atoms in the chain, $R^2$ denotes a $C_1$ to $C_4$ alkyl residue or hydrogen, $R^3$, $R^4$ and $R^5$ mutually independently denote hydrogen, a methyl residue or a $C_2$ to $C_4$ alkyl residue, n denotes an integer selected from 1, 2, 3, 4 or 5. More preferably, $R^2$ means a methyl or ethyl residue, n=2 and $R^3=R^4=$methyl or ethyl and $R^5$ denotes hydrogen. $R^1$ preferably denotes one of the residues caprinoyl, lauroyl, myristoyl, palmitoyl, stearoyl, oleoyl, linoloyl, arachinoyl, cetyloyl, behenoyl, eicosanoyl and/or 18-methyleicosanoyl.

No anion is shown in the structure represented above. This anion is formed by an acidic group of the protein hydrolysate. Since the acidic protein hydrolysates according to the invention may comprise a plurality of acidic groups, a plurality of the fatty acid amidoamine structures represented above are accordingly also ionically attached to the acidic groups.

The carboxy-terminal end of the acidic protein hydrolysates forms an ionic complex with the cationic or cationizable $C_8$ to $C_{40}$ fatty acid amidoamine. Examples of such compounds under the INCI name Cetearamidoethyl Diethonium Hydrolyzed Protein based on wheat or rice are commercially obtainable under the names Vegetamid® 18MEA R (Cetearamidoethyl Diethonium Hydrolyzed Rice) or Vegetamid® 18MEA G (Cetearamidoethyl Diethonium Hydrolyzed Wheat) from Seiwa Kasei.

The ionic complexes according to the invention of an acidic protein hydrolysate and a fatty acid amidoamine are present in the compositions according to the invention in a quantity of 0.01 to 10.0 wt. %, preferably of 0.01 to 7.5 wt. %, more preferably of 0.1 to 5.0 wt. % relative to the total composition.

It is preferred according to the invention for the compositions according to the invention furthermore to include at least one quaternary compound. The effectiveness of the agent according to the invention is further increased and the stability of the composition considerably promoted thereby.

Quaternary ammonium compounds are in principle monomeric cationic or amphoteric ammonium compounds, monomeric amines, aminoamides, polymeric cationic ammonium compounds and polymeric amphoteric ammonium compounds. Among the numerous possible quaternary ammonium compounds, the following groups have proven particularly suitable and are in each case individually used in a quantity of 0.1 to 10.0 wt. %. Neither more nor less than this quantity is used even if a mixture of different compounds of quaternary ammonium compounds is used.

Esterquats according to formula (Tkat1-2) form the first group.

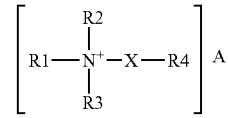

(Tkat1-2)

The residues $R^1$, $R^2$ and $R^3$ are here in each case mutually independent and may be identical or different. The residues $R^1$, $R^2$ and $R^3$ mean:
  a branched or unbranched alkyl residue with 1 to 4 carbon atoms which may include at least one hydroxyl group, or
  a saturated or unsaturated, branched or unbranched or a cyclic saturated or unsaturated alkyl residue with 6 to 30 carbon atoms which may include at least one hydroxyl group, or
  an aryl or alkaryl residue, for example phenyl or benzyl, the residue (—X—$R^4$), providing that at most 2 of the residues $R^2$ or $R^3$ may denote this residue:
The residue —(X—$R^4$) is present at least once to 3 times.
X here denotes:
1) —$(CH_2)_n$— with n=1 to 20, preferably n=1 to 10 and more preferably n=1-5, or
2) —$(CH_2$—$CHR^5$—$O)_n$— with n=1 to 200, preferably 1 to 100, more preferably 1 to 50, and more preferably 1 to 20 with $R^5$ meaning hydrogen, methyl or ethyl,
3) a hydroxyalkyl group with one to four carbon atoms which may be branched or unbranched and which includes at least one and at most 3 hydroxyl groups.

Examples of —X— are: —CHOH, —CHCH$_2$OH, —CH$_2$CHOH, —COHCHOH, —CHOHCOH, —CHCHOHCH$_3$, —CH$_2$COHCH$_3$, —CH$_2$CHOHCH$_2$—, —C(CH$_2$OH)$_2$, —CH$_2$CHOHCH$_2$OH, —CH$_2$CH$_2$CHOH, —CH$_2$COHCH$_3$ and hydroxybutyl residues, wherein the bond from —X— to R$^4$ extends from the free valence of the carbon atom in question and R$^4$ denotes:
1) R$^6$—O—CO—, in which R$^6$ is a saturated or unsaturated, branched or unbranched or a cyclic saturated or unsaturated alkyl residue with 6 to 30 carbon atoms which may include at least one hydroxyl group and which may optionally furthermore be ethoxylated with 1 to 100 ethylene oxide units and/or 1 to 100 propylene oxide units, or
2) R$^7$—CO—, in which R$^7$ is a saturated or unsaturated, branched or unbranched or a cyclic saturated or unsaturated alkyl residue with 6 to 30 carbon atoms which may include at least one hydroxyl group and which may optionally furthermore be ethoxylated with 1 to 100 ethylene oxide units and/or 1 to 100 propylene oxide units, and A denotes a physiologically acceptable organic or inorganic anion and is defined at this point as being representative for all the structures also described below. The anion of all the described cationic compounds is selected from the halide ions, fluoride, chloride, bromide or iodide, sulfates of general formula RSO$_3^-$, in which R has the meaning of saturated or unsaturated alkyl residues with 1 to 4 carbon atoms, or anionic residues of organic acids such as maleate, fumarate, oxalate, tartrate, citrate, lactate or acetate.

Such products are distributed for example under the trademarks Rewoquat®, Stepantex®, Dehyquart®, Armocare® and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90 and Akypoquat® 131 are examples of these esterquats.

Further compounds of formula (Tkat1-2) which are more preferred according to the invention belong to formula (Tkat1-2.1), the cationic betaine esters.

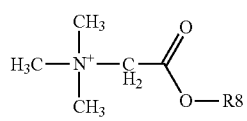

(Tkat1-2.1)

The meaning of R$^8$ corresponds to that of R$^7$.

More preferred esterquats are those with the trade names Armocare® VGH-70, and Dehyquart® F-75, Dehyquart® L80, Stepantex® VS 90 and Akypoquat® 131.

A further group are quaternary imidazoline compounds. The formula (Tkat2) illustrated below shows the structure of these compounds.

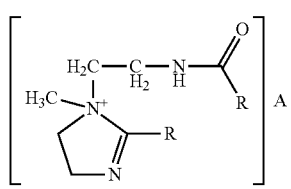

(Tkat2)

The residues R mutually independently in each case denote a saturated or unsaturated, linear or branched hydrocarbon residue with a chain length of 8 to 30 carbon atoms. The preferred compounds of formula (Tkat2) in each case include the identical hydrocarbon residue for R. The chain length of the residues R preferably amounts to 12 to 21 carbon atoms. A denotes an anion as previously described. Examples which are particularly according to the invention are obtainable for example under the INCI names Quaternium-27, Quaternium-72, Quaternium-83 and Quaternium-91. Quaternium-91 is highly preferred according to the invention.

In a more preferred embodiment of the invention, the agents according to the invention furthermore include at least one amine and/or cationized amine, in particular an amidoamine and/or a cationized amidoamine with the following structural formulae:

$$R^1—NH—(CH_2)_n—N^+R^2R^3R^4A \quad \text{(Tkat3)}$$

in which R$^1$ means an acyl or alkyl residue with 6 to 30 C atoms which may be branched or unbranched, saturated or unsaturated, and wherein the acyl residue and/or the alkyl residue may include at least one OH group, and R$^2$, R$^3$ and R$^4$ in each case mutually independently mean
1) hydrogen or
2) an alkyl residue with 1 to 4 C atoms which may be identical or different, saturated or unsaturated and
3) a branched or unbranched hydroxyalkyl group with one to 4 carbon atoms with at least one and at most three hydroxyl groups, for example —CH$_2$OH, —CH$_2$CH$_2$OH, —CHOHCHOH, —CH$_2$CHOHCH$_3$, —CH(CH$_2$OH)$_2$, —COH(CH$_2$OH)$_2$, —CH$_2$CHOHCH$_2$OH, —CH$_2$CH$_2$CH$_2$OH and hydroxybutyl residues, and
A means an anion as previously described and
n means an integer between 1 and 10.

A preferred composition is one in which the amine and/or the quaternized amine according to general formula (Tkat3) is an amidoamine and/or a quaternized amidoamine, in which R$^1$ means a branched or unbranched, saturated or unsaturated acyl residue with 6 to 30 C atoms which may include at least one OH group. A fatty acid residue obtained from oils and waxes, in particular from natural oils and waxes, is here preferred. Examples thereof which may be considered are lanolin, beeswax or candelilla wax.

Preferred amidoamines and/or quaternized amidoamines are also those in which R$^2$, R$^3$ and/or R$^4$ in formula (Tkat3) mean a residue according to general formula CH$_2$CH$_2$OR$^5$, in which R$^5$ may have the meaning of alkyl residues with 1 to 4 carbon atoms, hydroxyethyl or hydrogen. The preferred size of n in general formula (Tkat8) is an integer between 2 and 5.

The alkylamidoamines may both be present as such and be converted into a quaternary compound in the composition by protonation in an appropriately acidic solution. Cationic alkylamidoamines are preferred according to the invention.

Examples of such commercial products according to the invention are Witcamine® 100, Incromine® BB, Mackine® 401 and other Mackine® grades, Adogen® S18V, and, as permanently cationic aminoamines: Rewoquat® RTM 50, Empigen® CSC, Swanol® Lanoquat DES-50, Rewoquat® UTM 50, Schercoquat® BAS, Lexquat® AMG-BEO, or Incroquat® Behenyl HE.

The above-stated cationic surfactants may be used individually or in any desired combinations with one another, wherein quantities of between 0.01 and 10 wt. %, preferably quantities of 0.01 to 7.5 wt. % and particularly preferably quantities of 0.1 to 5.0 wt. % are present. The very best results are here obtained with quantities of 0.1 to 3.0 wt. % in each case relative to the total composition of the respective agent.

Further quaternary ammonium compounds are cationic and amphoteric polymers.

The cationic and/or amphoteric polymers may be homo- or copolymers or polymers based on natural polymers, wherein the quaternary nitrogen groups are present either in the polymer chain or preferably as substituents on one or more of the monomers. Monomers including ammonium groups may be copolymerized with non-cationic monomers. Suitable cationic monomers are unsaturated, free-radically polymerizable compounds which bear at least one cationic group, in particular ammonium-substituted vinyl monomers such as for example trialkylmethacryloxyalkylammonium, trialkylacryloxyalkylammonium, dialkyldiallylammonium and quaternary vinylammonium monomers with cyclic, cationic nitrogen-containing groups such as pyridinium, imidazolinium or quaternary pyrrolidones, for example alkylvinylimidazolium, alkylvinylpyridinium or alkylvinylpyrrolidone salts. The alkyl groups of these monomers are preferably lower alkyl groups such as for example $C_1$ to $C_7$ alkyl groups, more preferably $C_1$ to $C_3$ alkyl groups.

Monomers including ammonium groups may be copolymerized with non-cationic monomers. Suitable comonomers are for example acrylamide, methacrylamide; alkyl- and dialkylacrylamide, alkyl- and dialkylmethacrylamide, alkyl acrylate, alkyl methacrylate, vinylcaprolactone, vinylcaprolactam, vinylpyrrolidone, vinyl esters, for example vinyl acetate, vinyl alcohol, propylene glycol or ethylene glycol, wherein the alkyl groups of these monomers are preferably $C_1$ to $C_7$ alkyl groups, more preferably $C_1$ to $C_3$ alkyl groups.

Among the numerous polymers of this kind, the following have proven to be particularly effective components of the active substance complex according to the invention:
Homopolymers of the general formula

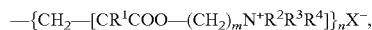

in which $R^1$=—H or —$CH_3$, $R^2$, $R^3$ and $R^4$ are mutually independently selected from $C_{1-4}$ alkyl, alkenyl or hydroxyalkyl groups, m=1, 2, 3 or 4, n is a natural number and $X^-$ is a physiologically acceptable organic or inorganic anion. In the context of these polymers, those which are preferred according to the invention are those for which at least one of the following conditions applies: $R^1$ denotes a methyl group, $R^2$, $R^3$ and $R^4$ denote methyl groups, m has the value 2.

Physiologically acceptable counterions $X^-$ which may, for example, be considered are halide ions, sulfate ions, phosphate ions, methosulfate ions and organic ions such as lactate, citrate, tartrate and acetate ions. Methosulfate and halide ions, in particular chloride, are preferred.

An amphoteric polymer which is highly preferred according to the invention is a copolymer which is of the following composition: 0.1 to 50% (relative to the total number of monomers in the copolymer) monomers of formula (I)

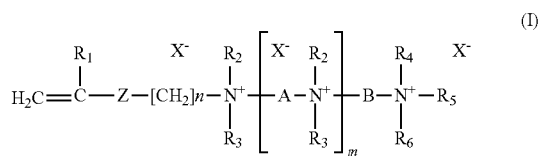

in which the definitions of the residues $R^1$, $R^2$, $R^3$, $R^4$, $R^5$, $R^6$ and of the indices n, m and the groups Z, A, B, X stated further above apply, and monomers from the group acrylic acid, methacrylic acid, alpha-ethacrylic acid, beta,beta-dimethylacrylic acid, methylenemalonic acid, vinylacetic acid, allylacetic acid, ethylideneacetic acid, propylideneacetic acid, crotonic acid, maleic acid, fumaric acid, itaconic acid, citraconic acid, mesaconic acid, N-methacryloylalanine, N-acryloylhydroxyglycine, sulfopropyl acrylate, sulfoethyl acrylate, sulfoethyl methacrylate, sulfoethyl methacrylate, styrenesulfonic acid, vinylsulfonic acid, vinylphosphonic acid, phosphoethyl acrylate, phosphonoethyl acrylate, phosphopropyl acrylate, phosphonopropyl acrylate, phosphoethyl methacrylate, phosphonoethyl methacrylate, phosphopropyl methacrylate and phosphonopropyl methacrylate and the alkali metal and ammonium salts of these acids, and optionally nonionic monomers from the group acrylamide, vinyl alcohol, $C_1$-$C_4$ alkyl esters of acrylic acid and/or of methacrylic acid, $C_1$-$C_4$ hydroxyalkyl esters of acrylic acid and/or of methacrylic acid, in particular ethylene glycol and propylene glycol acrylate and methacrylate, polyalkoxylated esters of acrylic acid and/or of methacrylic acid, in particular polyethylene glycol and polypropylene glycol esters, esters of acrylic acid and/or of methacrylic acid with polyethylene glycol or polypropylene glycol mono-($C_1$-$C_{25}$)-alkyl ethers, vinyl acetate, vinylpyrrolidone and methyl vinyl ether, wherein monomers A2 and A3 together constitute 50 to 99.9% (relative to the total number of monomers in the copolymer) of the copolymer.

In formula (I) for monomer (A), $R^1$ is preferably a methyl group, and $R^2$, $R^3$, $R^4$, $R^5$ and $R^6$ also denote methyl groups. The group Z is preferably an —NH group, the index n more preferably denotes the number 3.

Depending on the groups A and B selected and the index m, various monomers of formula (I) may be preferred. A preferred monomer which complies with the criteria set out in the above-stated paragraph furthermore has a —$CH_2$—CH(OH)—$CH_2$ group as group B, and the index m denotes the number 0. Polymers which are preferred according to the invention are composed of monomers A1)
A1) 0.1 to 50%, preferably 10 to 50% (relative to the total number of monomers in the copolymer) of monomers of formula (Ia)

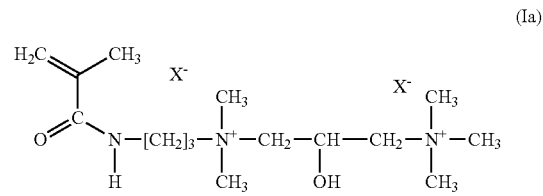

in which
X denotes chloride, sulfate, methosulfate,
and the monomers A2) from the group acrylic acid, methacrylic acid and the alkali metal and ammonium salts of these acids,
wherein monomer A2 constitutes 50 to 99.9%, preferably 50 to 90% (relative to the total number of monomers in the copolymer) of the copolymer.

A further preferred monomer which complies with the criteria set out in the above-stated paragraph furthermore has a —$CH_2$—CH(OH)—$CH_2$ group as group B, a —$(CH_2)_2$ or a —$(CH_2)_3$ or a —$(CH_2)_4$ group as group A, and index in denotes the number 1. In these polymers which include such monomers, at least one copolymer A is selected from:

A1) 0.1 to 50%, preferably 10 to 50% (relative to the total number of monomers in the copolymer) of monomers of formula (Ib)

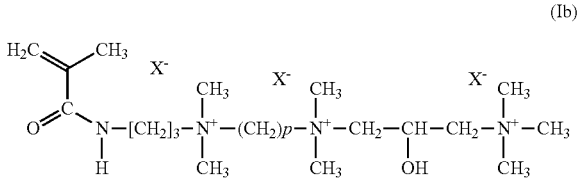

(Ib)

in which
p denotes 2, 3 or 4,
X denotes chloride, sulfate, methosulfate,
A2) monomers from the group acrylic acid, methacrylic acid and the alkali metal and ammonium salts of these acids,
wherein monomer A2 constitutes 50 to 99.9%, preferably 50 to 90% (relative to the total number of monomers in the copolymer) of the copolymer.

More preferred monomers A2 are acrylic acid or the salts thereof (also mixed, i.e. partially neutralized acrylic acids) and acrylamide. A preferred copolymer A is a copolymer of the monomer (Ia), sodium acrylate and acrylamide, wherein the following distribution (in % of the total monomers present in the polymer) is preferred:
monomer (Ia): 0.1 to 50%, preferably 10 to 50%
sodium acrylate: 10 to 95%, preferably 50 to 70%
acrylamide: 0 to 50%, preferably 0 to 30%

A preferred copolymer A preferably includes the following number of the respective monomers:
monomer (Ia): values of 1 to 12500, preferably of 2 to 8000, more preferably of 3 to 4000 and in particular of 5 to 2000
sodium acrylate: values of 1 to 24000, preferably of 5 to 15000, more preferably of 10 to 10000 and in particular of 100 to 4800
acrylamide: values 0, 1, 2, 3, 4, 5, wherein the value 0 is preferred.

To summarize, amphoteric polymers according to the invention are more preferred if they include at least one copolymer A of the general formula (Ic)

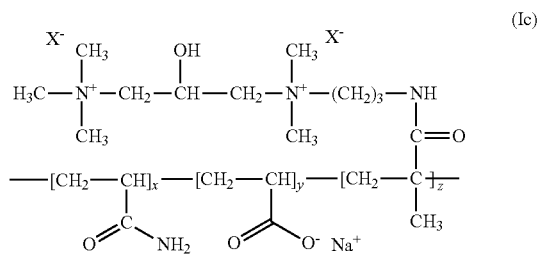

(Ic)

in which:

$x+y+z=Q$

Q denotes values from 3 to 55000, preferably from 10 to 25000, more preferably from 50 to 15000, further preferably from 100 to 10000, still more preferably from 500 to 8000 and in particular from 1000 to 5000,
x denotes (0 to 0.5) Q, preferably (0 to 0.3) Q and in particular the values 0, 1, 2, 3, 4, 5, wherein the value 0 is preferred,
y denotes (0.1 to 0.95) Q, preferably (0.5 to 0.7) Q and in particular values from 1 to 24000, preferably from 5 to 15000, more preferably from 10 to 10000 and in particular from 100 to 4800,
z denotes (0.001 to 0.5) Q, preferably (0.1 to 0.5) Q and in particular values from 1 to 12500, preferably from 2 to 8000, more preferably from 3 to 4000 and in particular from 5 to 2000.

In addition to or instead of the above-stated copolymer, the agents according to the invention may also include a copolymer which is synthesized from monomers of formula (Ia), maleic or fumaric acid (or the disodium salts thereof) and acrylamide. The following distribution (in % of the total monomers present in the polymer) is here preferred:
monomer (Ia): 0.1 to 50%, preferably 10 to 50%
maleic acid or fumaric acid (or the disodium salt thereof): 10 to 95%, preferably 50 to 70%
acrylamide: 0 to 50%, preferably 0 to 30%.

A preferred copolymer A preferably includes the following number of the respective monomers:
monomer (Ia): values of 1 to 12500, preferably of 2 to 8000, more preferably of 3 to 4000 and in particular of 5 to 2000
maleic acid or fumaric acid (or the disodium salt thereof): values of 1 to 24000, preferably of 5 to 15000, more preferably of 10 to 10000 and in particular of 100 to 4800
acrylamide: values 0, 1, 2, 3, 4, 5, wherein the value 0 is preferred.

One highly preferred polymer which is of the above-described structure is commercially obtainable under the name Polyquaternium-74.

One particularly suitable homopolymer is poly(methacryloyloxyethyltrimethylammonium chloride), which may if desired be crosslinked, with the INCI name Polyquaternium-37. Such products are commercially obtainable for example under the names Rheocare® CTH (Cosmetic Rheologies) and Synthalen® CR (3V Sigma).

The homopolymer is preferably used in the form of a nonaqueous polymer dispersion. Such polymer dispersions are commercially obtainable under the names Salcare® SC 95 and Salcare® SC 96.

Suitable cationic polymers which are derived from natural polymers are cationic derivatives of polysaccharides, for example cationic derivatives of cellulose, starch or guar. Chitosan and chitosan derivatives are furthermore suitable. Cationic polysaccharides have the general formula

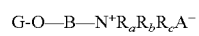

G is an anhydroglucose residue, for example starch or cellulose anhydroglucose;
B is a divalent linking group, for example alkylene, oxyalkylene, polyoxyalkylene or hydroxyalkylene;
$R_a$, $R_b$ and $R_c$ are mutually independently alkyl, aryl, alkylaryl, arylalkyl, alkoxyalkyl or alkoxyaryl in each case with up to 18 C atoms, wherein the total number of C atoms in $R_a$, $R_b$ and $R_c$ preferably amounts to at most 20;
$X^-$ is a conventional counteranion and is preferably chloride.

Cationic, thus quaternized, celluloses are commercially obtainable with different degrees of substitution, cationic charge densities, nitrogen contents and molecular weights. For example, Polyquaternium-67 is commercially offered for sale under the names Polymer® SL or Polymer® SK (Amerchol). A further highly preferred cellulose is offered for sale under the trade name Mirustyle® CP from Croda. This is a trimonium and cocodimonium hydroxyethylcellulose as a derivatized cellulose with the INCI name Polyquaternium-72. Polyquaternium-72 may be used both in solid form and already predissolved in aqueous solution.

Further cationic celluloses are known by the names Polymer JR® 400 (Amerchol, INCI name Polyquaternium-10) and Polymer Quatrisoft® LM-200 (Amerchol, INCI name Polyquaternium-24). Further commercial products are the compounds Celquat® H 100 and Celquat® L 200. Finally a further derivatized cellulose with the INCI name Polyquaternium-72 is obtainable from Croda under the trade name Mirustyle® CP with Trimonium and Cocodimonium Hydroxyethylcellulose. Polyquaternium-72 may be used both in solid form and already predissolved in aqueous solution. More preferred cationic celluloses are Polyquatemium-10, Polyquaternium-24, Polyquaternium-67 and Polyquatemium-72.

Suitable cationic guar derivatives are distributed under the trade name Jaguar® and have the INCI name Guar Hydroxypropyltrimonium Chloride. Particularly suitable cationic guar derivatives are furthermore also commercially obtainable from Hercules under the name N-Hance®. Further cationic guar derivatives are distributed by Cognis under the name Cosmedia®. One preferred cationic guar derivative is the commercial product AquaCat® from Hercules. This raw material is an already predissolved cationic guar derivative. Cationic guar derivatives are preferred according to the invention.

One suitable chitosan is for example distributed by Kyowa Oil & Fat, Japan, under the tradename Flonac®. One preferred chitosan salt is chitosoniumpyrrolidone carboxylate, which is for example distributed by Amerchol, USA, under the name Kytamer® PC. Further chitosan derivatives are readily commercially obtainable under the trade names Hydagen® CMF, Hydagen® HCMF and Chitolam® NB/101.

Further preferred cationic polymers are for example
cationic alkyl polyglycosides,
cationized honey, for example the commercial product Honeyquat® 50,
polymeric dimethyldiallylammonium salts and the copolymers thereof with esters and amides of acrylic acid and methacrylic acid. The products commercially obtainable under the names Merquat®100 (poly(dimethyldiallylammonium chloride)) and Merquat®550 (dimethyldiallylammonium chloride-acrylamide copolymer) are examples of such cationic polymers with the INCI name Polyquaternium-7,
vinylpyrrolidone-vinylimidazolium methochloride copolymers, as are offered for sale under the names Luviquat® FC 370 and FC 550 and the INCI name Polyquatemium-16 together with FC 905 and HM552,
quaternized vinylpyrrolidone/dimethylaminoethyl methacrylate, for example vinylpyrrolidone/dimethylaminoethylmethacrylate methosulfate copolymer, which is distributed by Gaf Co., USA under the trade names Gafquat® 755 N and Gafquat® 734 and the INCI name Polyquatemium-11,
quaternized polyvinyl alcohol,
and the polymers known by the names Polyquaternium-2, Polyquatemium-17, Polyquatemium-18 and Polyquaternium-27 with quaternary nitrogen atoms in the polymer main chain,
vinylpyrrolidone-vinylcaprolactam-acrylate terpolymers, as are for example offered for sale with acrylic acid esters and acrylamides as the third monomeric building block under the name Aquaflex® SF 40.

Amphoteric polymers according to the invention are those polymers in which a cationic group is derived from at least one of the following monomers:
(i) monomers with quaternary ammonium groups of general formula (Mono1),

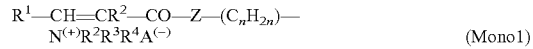

in which $R^1$ and $R^2$ mutually independently denote hydrogen or a methyl group and $R^3$, $R^4$ and $R^5$ mutually independently denote alkyl groups with 1 to 4 carbon atoms, Z is an NH group or an oxygen atom, n is an integer from 2 to 5 and $A^{(-)}$ is the anion of an organic or inorganic acid, (ii) monomers with quaternary ammonium groups of general formula (Mono2),

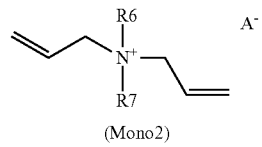

in which $R^6$ and $R^7$ mutually independently denote a ($C_1$ to $C_4$) alkyl group, in particular a methyl group and $A^-$ is the anion of an organic or inorganic acid, (iii) monomeric carboxylic acids of general formula (Mono3),

in which $R^8$ and $R^9$ are mutually independently hydrogen or methyl groups.

More preferred polymers are those in which monomers of type (i) are used, in which $R^3$, $R^4$ and $R^5$ are methyl groups, Z is an NH group and $A^{(-)}$ a halide, methoxysulfate or ethoxysulfate ion; acrylamidopropyltrimethylammonium chloride is a more preferred monomer (i). Acrylic acid is preferably used as monomer (ii) for the stated polymers.

More preferred amphoteric polymers are copolymers prepared from at least one monomer (Mono1) or (Mono2) with the monomer (Mono3), in particular copolymers prepared from monomers (Mono2) and (Mono3). Amphoteric polymers which are particularly preferably used according to the invention are copolymers of diallyldimethylammonium chloride and acrylic acid. These copolymers are distributed under the INCI name Polyquatemium-22, inter alia with the trade name Merquat® 280 (Nalco).

Apart from a monomer (Mono1) or (Mono2) and a monomer (Mono3), amphoteric polymers according to the invention may furthermore additionally include a monomer (Mono4)
(iv) monomeric carboxamides of general formula (Mono4),

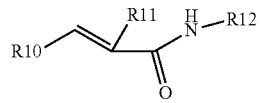

in which $R^{10}$ and $R^{11}$ are mutually independently hydrogen or methyl groups and $R^{12}$ denotes a hydrogen atom or a ($C_1$ to $C_8$) alkyl group.

Amphoteric polymers based on a comonomer (Mono4) which are particularly preferably used according to the invention are terpolymers of diallyldimethylammonium chloride, acrylamide and acrylic acid. These copolymers are distributed under the INCI name Polyquatemium-39, inter alia with the trade name Merquat® Plus 3330 (Nalco).

The amphoteric polymers may generally be used according to the invention both directly and in salt form, which is obtained by neutralization of the polymers, for example with an alkali metal hydroxide.

The above-stated cationic polymers may be used individually or in any desired combinations with one another, wherein quantities of between 0.01 and 10 wt. %, preferably quantities of 0.01 to 7.5 wt. % and particularly preferably quantities of 0.1 to 5.0 wt. % are present. The very best results are here obtained with quantities of 0.1 to 3.0 wt. % in each case relative to the total composition of the respective agent.

The present invention accordingly firstly provides a hair treatment agent including in a suitable cosmetic carrier, in each case relative to the total weight of the composition of the agent
a) at least one amino acid in a total quantity of 0.01 to 10.0 wt. %,
b) at least one cationic aminosilicone with at least three terminal amino-functional groups in a total quantity of 0.01 to 5.0 wt. % and
c) at least one quaternary ammonium compound in a total quantity of 0.1 to 10.0 wt. % relative to the weight of the total composition, selected from at least one of the groups
  i. of esterquats and/or
  ii. of quaternary imidazolines of formula (Tkat2),

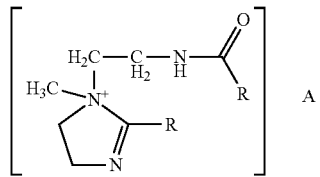

in which the residues R mutually independently in each case denote a saturated or unsaturated, linear or branched hydrocarbon residue with a chain length of 8 to 30 carbon atoms and A denotes a physiologically acceptable anion, and/or
  iii. of amines and/or cationized amines and/or
  iv. poly(methacryloyloxyethyltrimethylammonium) compounds and/or;
  v. quaternized cellulose derivatives, in particular Polyquatemium-10, Polyquaternium-24, Polyquatemium-27, Polyquaternium-67, Polyquaternium-72, and/or
  vi. cationic alkyl polyglycosides and/or
  vii. cationized honey and/or
  viii. cationic guar derivatives and/or
  ix. chitosan and/or
  x. polymeric dimethyldiallylammonium salts and the copolymers thereof with esters and amides of acrylic acid and methacrylic acid, in particular Polyquaternium-7 and/or
  xi. copolymers of vinylpyrrolidone with quaternized derivatives of dialkylaminoalkyl acrylate and methacrylate, in particular Polyquaternium-11 and/or
  xii. vinylpyrrolidone-vinylimidazolium methochloride copolymers, in particular Polyquaternium-16 and/or
  xiii. quaternized polyvinyl alcohol and/or
  xiv. Polyquatemium-74,
and mixtures thereof.

Preferred ingredients of group c) are Stearamidopropyldimethylamine and/or Distearoylethyl Hydroxyethylmonium Methosulfate and/or Dicocoyl Hydroxyethylmonium Methosulfate and/or Dipalmitoylethyl Dimonium Chloride and/or Quaternium-27 and/or Quaternium-91 and/or Behenoyl PG-Trimonium Chloride. It is furthermore highly preferred to select at least two, still more preferably at least three ingredients from this group. It is highly preferred in these mixtures for one of the two or three compounds to be Stearamidopropyldimethylamine. It is most highly preferred for Cetyltrimethylammonium Chloride or Behenyltrimethylammonium Chloride furthermore to be added as an optional cationic ammonium compound. The best results are, however, in particular achieved if the latter-stated compositions including Stearamidopropyldimethylamine and Distearoylethyl Hydroxyethylmonium Methosulfate and/or Dicocoyl Hydroxyethylmonium Methosulfate and/or Dipalmitoylethyl Dimonium Chloride and/or Quaternium-27 and/or Quaternium-91 and/or Behenoyl PG-Trimonium Chloride and Cetyltrimethylammonium Chloride or Behenyltrimethylammonium Chloride furthermore include one of the above-stated cationic polymers, in particular poly(methacryloyloxyethyltrimethylammonium) compounds and/or; quaternized cellulose derivatives, in particular Polyquatemium-10, Polyquaternium-24, Polyquaternium-27, Polyquatemium-67, Polyquaternium-72, and/or Polyquaternium-74. Polyquaternium-67, Polyquaternium-72 and Polyquaternium-74 are here most preferred.

Compositions which are more preferred according to the invention are those which contain:
a) alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, thyroxine, tryptophan, tyrosine, valine, betaine, ornithine, 1,1-dimethylproline, hercynine (Nα,Nα,Nα-trimethyl-L-histidine betaine), ergothioneine (thioneine, 2-mercapto-Nα,Nα,Nα-trimethyl-L-histidine betaine), carnitine, taurine and choline and mixtures thereof, and
b) Silicone Quaternium-22 and
c) Stearamidopropyldimethylamine and Distearoylethyl Hydroxyethylmonium Methosulfate and/or Dicocoyl Hydroxyethylmonium Methosulfate and/or Dipalmitoylethyl Dimonium Chloride and Quaternium-27 and/or Quaternium-91 and/or Behenoyl PG-Trimonium Chloride and Cetyltrimethylammonium Chloride or Behenyltrimethylammonium Chloride and furthermore poly(methacryloyloxyethyltrimethylammonium) compounds and/or Polyquaternium-67 and/or Polyquatemium-72 and/or Polyquaternium-74.

It is furthermore highly preferable according to the invention for the compositions according to the invention to include at least one amphoteric and/or zwitterionic surfactant. These compounds possibly contribute substantially to the stability of the cosmetic compositions.

Particularly suitable zwitterionic surfactants are "betaines" such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines with in each case 8 to 18 C atoms in the alkyl or acyl group and cocoacylaminoethylhydroxyethylcarboxymethyl glycinate. One preferred zwitterionic surfactant is the fatty acid amide derivative known by the INCI name Cocamidopropyl Betaine.

Ampholytic surfactants (Tampho) are taken to mean those surface-active compounds which are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approximately 8 to 24 C atoms in the alkyl group. Typical examples of amphoteric or zwitterionic surfactants are alkylbetaines, alkylamidobetaines, aminopropionates, aminoglycinates, imidazolinium betaines and sulfobetaines.

More preferred ampholytic surfactants are N-cocoalkyl aminopropionate, cocoacylaminoethyl aminopropionate and $C_{12-18}$ acyl sarcosine. One more preferred compound is Coco Betaine.

These ingredients are used in quantities of 0.01 to 8.0 wt. % relative to the total composition of the agent. Quantities of 0.05 to 7.0 wt. % are here preferred. Quantities of 0.1 to 6.0 wt. % are more preferred and quantities of 0.3 to 3.0 wt. % are highly preferred.

The present invention accordingly thirdly provides a hair treatment agent including in a suitable cosmetic carrier, in each case relative to the total composition of the agent
a) at least one amino acid in a total quantity of 0.01 to 10.0 wt. %,
b) at least one cationic aminosilicone with at least three terminal amino-functional groups in a total quantity of 0.01 to 5.0 wt. % and
c) at least one quaternary ammonium compound in a total quantity of 0.1 to 10.0 wt. % relative to the weight of the total composition, selected from at least one of the groups
i. of esterquats and/or
ii. of quaternary imidazolines of formula (Tkat2),

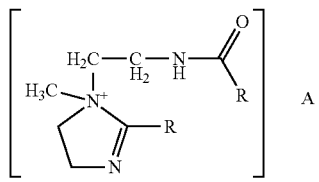

in which the residues R mutually independently in each case denote a saturated or unsaturated, linear or branched hydrocarbon residue with a chain length of 8 to 30 carbon atoms and A denotes a physiologically acceptable anion, and/or
iii. of amines and/or cationized amines and/or
iv. poly(methacryloyloxyethyltrimethylammonium) compounds and/or;
v. quaternized cellulose derivatives, in particular Polyquaternium-10, Polyquaternium-24, Polyquaternium-27, Polyquaternium-67, Polyquaternium-72, and/or
vi. cationic alkyl polyglycosides and/or
vii. cationized honey and/or
viii. cationic guar derivatives and/or
ix. chitosan and/or
x. polymeric dimethyldiallylammonium salts and the copolymers thereof with esters and amides of acrylic acid and methacrylic acid, in particular Polyquaternium-7 and/or
xi. copolymers of vinylpyrrolidone with quaternized derivatives of dialkylaminoalkyl acrylate and methacrylate, in particular Polyquaternium-11 and/or
xii. vinylpyrrolidone-vinylimidazolium methochloride copolymers, in particular Polyquatemium-16 and/or
xiii. quaternized polyvinyl alcohol and/or
xiv. Polyquaternium-74.
d) 0.01 wt. % to 8.0 wt. % of at least one surfactant selected from zwitterionic and/or amphoteric surfactants.

More preferred compositions of this embodiment include as ingredients of group c) Stearamidopropyldimethylamine and/or Distearoylethyl Hydroxyethylmonium Methosulfate and/or Dicocoyl Hydroxyethylmonium Methosulfate and/or Dipalmitoylethyl Dimonium Chloride and/or Quaternium-27 and/or Quaternium-91 and/or Behenoyl PG-Trimonium Chloride. It is furthermore highly preferred to select at least two, still more preferably at least three ingredients from this group. It is highly preferred in these mixtures for one of the two or three compounds to be Stearamidopropyldimethylamine. It is most highly preferred for Cetyltrimethylammonium Chloride or Behenyltrimethylammonium Chloride furthermore to be added as an optional cationic ammonium compound. The best results are, however, in particular achieved if the latter-stated compositions including Stearamidopropyldimethylamine and Distearoylethyl Hydroxyethylmonium Methosulfate and/or Dicocoyl Hydroxyethylmonium Methosulfate and/or Dipalmitoylethyl Dimonium Chloride and/or Quaternium-27 and/or Quaternium-91 and/or Behenoyl PG-Trimonium Chloride and Cetyltrimethylammonium Chloride or Behenyltrimethylammonium Chloride furthermore include one of the likewise above-stated cationic polymers, in particular poly(methacryloyloxyethyltrimethylammonium) compounds and/or; quaternized cellulose derivatives, in particular Polyquaternium-10, Polyquaternium-24, Polyquatemium-27, Polyquaternium-67, Polyquaternium-72, and/or Polyquaternium-74. Polyquaternium-67, Polyquaternium-72 and Polyquaternium-74 are here most preferred.

Compositions which are more preferred according to the invention are those which contain:
a) arginine, glutamine, carnitine and taurine and mixtures of arginine and taurine,
glutamine and taurine,
glutamine and carnitine,
arginine and glutamine,
carnitine and taurine, and mixtures of arginine, carnitine and taurine,
glutamine, carnitine and taurine,
b) Silicone Quaternium-22 and
c) Stearamidopropyldimethylamine and Distearoylethyl Hydroxyethylmonium Methosulfate and/or Dicocoyl Hydroxyethylmonium Methosulfate and/or Dipalmitoylethyl Dimonium Chloride and Quaternium-27 and/or Quaternium-91 and/or Behenoyl PG-Trimonium Chloride and Cetyltrimethylammonium Chloride or Behenyltrimethylammonium Chloride and furthermore poly(methacryloyloxyethyltrimethylammonium) compounds and/or Polyquaternium-67 and/or Polyquaternium-72 and/or Polyquaternium-74 and
d) Cocamidopropyl Betaine and/or Coco Betaine.

Any ingredients conventional in cosmetic compositions may furthermore be added to this highly preferred ingredient parent structure.

In addition to the mandatory silicones previously described, the compositions according to the invention may include further silicones. These optional silicones are preferably at least one silicone polymer selected from the group of dimethiconols and/or the group of amino-functional silicones and/or the group of dimethicones and/or the group of cyclomethicones.

The dimethicones according to the invention may be both linear and branched and cyclic or cyclic and branched. Linear dimethicones may be represented by the following structural formula (Si1):

$$(SiR^1{}_3)-O-(SiR^2{}_2-O-)_x-(SiR^1{}_3)(SM)$$

Branched dimethicones may be represented by the structural formula (Si1.1):

$$\begin{array}{c}\text{(Si1.1)}\\[2pt]
\text{R1}\!-\!\underset{\underset{\text{R1}}{|}}{\overset{\overset{\text{R1}}{|}}{\text{Si}}}\!-\!\text{O}\!-\!\!\Big(\!\underset{\underset{\text{R2}}{|}}{\overset{\overset{\text{R2}}{|}}{\text{Si}}}\!-\!\text{O}\!\Big)_{\!x}\!\underset{\underset{\text{O}}{|}}{\overset{\overset{\text{R2}}{|}}{\text{Si}}}\!-\!\text{O}\!-\!\!\Big(\!\underset{\underset{\text{R2}}{|}}{\overset{\overset{\text{R2}}{|}}{\text{Si}}}\!-\!\text{O}\!\Big)_{\!y}\!\underset{\underset{\text{R1}}{|}}{\overset{\overset{\text{R1}}{|}}{\text{Si}}}\!-\!\text{R1}\\[2pt]
[\text{R2}-\underset{\underset{\text{R2}}{|}}{\overset{\overset{}{|}}{\text{Si}}}-\text{O}]_z-\underset{\underset{\text{R1}}{|}}{\overset{\overset{\text{R1}}{|}}{\text{Si}}}-\text{R1}\end{array}$$

The residues $R^1$ and $R^2$ mutually independently in each case denote hydrogen, a methyl residue, a $C_2$ to $C_{30}$ linear, saturated or unsaturated hydrocarbon residue, a phenyl residue and/or an aryl residue. The numbers x, y and z are integers and in each case mutually independently range from 0 to 50,000. The molar weights of the dimethicones are between 1000 D and 10000000 D. Viscosities are between 100 and 10000000 cPs measured at 25° C. with the assistance of a glass capillary viscometer using the Dow Corning Corporate Test Method CTM 0004 of 20 Jul. 1970. Preferred viscosities are between 1000 and 5000000 cPs, particularly preferred viscosities are between 10000 and 3000000 cPs. The most preferred range is between 50000 and 2000000 cPs. Viscosities around the range of approximately 60,000 cPs are highly preferred. Reference may be made by way of example to the product "Dow Corning 200, 60000 cSt".

More preferred cosmetic or dermatological preparations according to the invention are characterized in that they include at least one silicone of formula (Si1.2)

$$(CH_3)_3Si-[O-Si(CH_3)_2]_x-O-Si(CH_3)_3 \quad\text{(Si1.2)},$$

in which x denotes a number from 0 to 100, preferably from 0 to 50, further preferably from 0 to 20 and in particular from 0 to 10.

The dimethicones (Si1) are present in the compositions according to the invention in quantities of 0.01 to 10 wt. %, preferably 0.01 to 8 wt. %, more preferably 0.1 to 7.5 wt. % and in particular 0.1 to 5 wt. % relative to the total composition.

Finally, silicone compounds are taken to mean dimethiconols (Si8). The dimethiconols according to the invention may be both linear and branched and cyclic or cyclic and branched. Linear dimethiconols may be represented by the following structural formula (Si8-I):

$$(SiOHR^1{}_2)-O-(SiR^2{}_2-O-)_x-(SiOHR^1{}_2) \quad\text{(Si8-I)}$$

Branched dimethiconols may be represented by the structural formula (Si8-II):

$$\begin{array}{c}\text{(Si8-II)}\\[2pt]
\text{HO}\!-\!\underset{\underset{\text{R1}}{|}}{\overset{\overset{\text{R1}}{|}}{\text{Si}}}\!-\!\text{O}\!-\!\!\Big(\!\underset{\underset{\text{R2}}{|}}{\overset{\overset{\text{R2}}{|}}{\text{Si}}}\!-\!\text{O}\!\Big)_{\!x}\!\underset{\underset{\text{O}}{|}}{\overset{\overset{\text{R2}}{|}}{\text{Si}}}\!-\!\text{O}\!-\!\!\Big(\!\underset{\underset{\text{R2}}{|}}{\overset{\overset{\text{R2}}{|}}{\text{Si}}}\!-\!\text{O}\!\Big)_{\!y}\!\underset{\underset{\text{R1}}{|}}{\overset{\overset{\text{R1}}{|}}{\text{Si}}}\!-\!\text{OH}\\[2pt]
[\text{R2}-\underset{\underset{\text{R2}}{|}}{\overset{\overset{}{|}}{\text{Si}}}-\text{O}]_z-\underset{\underset{\text{R1}}{|}}{\overset{\overset{\text{R1}}{|}}{\text{Si}}}-\text{OH}\end{array}$$

The residues $R^1$ and $R^2$ mutually independently denote in each case hydrogen, a methyl residue, a $C_2$ to $C_{30}$ linear, saturated or unsaturated hydrocarbon residue, a phenyl residue and/or an aryl residue. The numbers x, y and z are integers and in each case mutually independently range from 0 to 50,000. The molar weights of the dimethiconols are between 1000 D and 10000000 D. Viscosities are between 100 and 10000000 cPs measured at 25° C. with the assistance of a glass capillary viscometer using the Dow Corning Corporate Test Method CTM 0004 of 20 Jul. 1970. Preferred viscosities are between 1000 and 5000000 cPs, particularly preferred viscosities are between 10000 and 3000000 cPs. The most preferred range is between 50000 and 2000000 cPs.

The following commercial products can be mentioned as examples of such products: Dow Corning 1-1254 Fluid, Dow Corning 2-9023 Fluid, Dow Corning 2-9026 Fluid, Abil OSW 5 (Degussa Care Specialties), Dow Corning 1401 Fluid, Dow Corning 1403 Fluid, Dow Corning 1501 Fluid, Dow Corning 1784 HVF Emulsion, Dow Corning 9546 Silicone Elastomer Blend, SM555, SM2725, SM2765, SM2785 (all above-stated from GE Silicones), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all above-stated from Wacker-Chemie GmbH).

The dimethiconols (Si8) are in the compositions according to the invention in quantities of 0.01 to 10 wt. %, preferably 0.01 to 8 wt. %, more preferably 0.1 to 7.5 wt. % and in particular 0.1 to 5 wt. % of dimethiconol relative to the composition.

More preferred agents according to the invention include one or more amino-functional silicones. Such silicones may, for example, be described by the formula (Si-2)

$$M(R_aQ_bSiO_{(4-a-b)/2})_x(RcSiO_{(4-c)/2})_yM \quad\text{(Si-2)}$$

wherein in the above formula

R is a hydrocarbon or a hydrocarbon residue with 1 to approximately 6 carbon atoms, Q is a polar residue of the general formula $-R^1HZ$, in which $R^1$ is a divalent linking group which is attached to hydrogen and the residue Z and is composed of carbon and hydrogen atoms, carbon, hydrogen and oxygen atoms or carbon, hydrogen and nitrogen atoms, and Z is an organic, amino-functional residue which includes at least one amino-functional group;

a assumes values in the range from approximately 0 to approximately 2, b assumes values in the range from approximately 1 to approximately 3, a+b is less than or equal to 3, and c is a number in the range from approximately 1 to approximately 3, and x is a number in the range from 1 to approximately 2,000, preferably from approximately 3 to approximately 50 and most preferably from approximately 3 to approximately 25, and y is a number in the range from approximately 20 to approximately 10,000, preferably from approximately 125 to approximately 10,000 and most preferably from approximately 150 to approximately 1,000, and M is a suitable silicone end group as known from the prior art, preferably trimethylsiloxy.

According to formula (Si-2), Z is an organic, amino-functional residue including at least one functional amino group. One possible formula for said Z is $NH(CH_2)_zNH_2$, in which z is an integer greater than or equal to 1. Another possible formula for said Z is —NH(CH$_2$)$_z$(CH$_2$)$_{zz}$NH, in which both z and zz are mutually independently an integer greater than or equal to 1, wherein this structure comprises diamino ring structures, such as piperazinyl. Said Z is most preferably an —NHCH$_2$CH$_2$NH$_2$ residue. Another possible formula for said Z is —N(CH$_2$)$_z$(CH$_2$)$_{zz}$NX$_2$ or —NX$_2$, in which each X of X$_2$ is independently selected from the group consisting of hydrogen and alkyl groups with 1 to 12 carbon atoms, and zz is 0.

Q according to formula (Si-2) is most preferably a polar amino-functional residue of formula —CH$_2$CH$_2$CH$_2$NHCH$_2$CH$_2$NH$_2$.

In formula (Si-2), a assumes values in the range from 0 to 2, b assumes values in the range from 2 to 3, a+b is less than or equal to 3, and c is a number in the range from 1 to 3. Cationic silicone oils which are suitable according to the invention are for example the commercially obtainable products Dow Corning (DC) 929 Emulsion, DC 2-2078, DC 5-7113, SM-2059 (General Electric) and SLM-55067 (Wacker).

More preferred agents according to the invention are characterized in that they include at least one amino-functional silicone of formula (Si3-a)

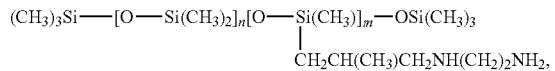

(Si-3a)

in which m and n are numbers, the sum of which (m+n) amounts to between 1 and 2000, preferably between 50 and 150, wherein n preferably assumes values from 0 to 1999 and in particular from 49 to 149 and m preferably assumes values from 1 to 2000, in particular from 1 to 10.

According to the INCI declaration, these silicones are designated trimethylsilylamodimethicones and are obtainable for example under the name Q2-7224 (manufacturer: Dow Corning; a stabilized trimethylsilylamodimethicone).

Agents according to the invention which are more preferred are also those which include at least one amino-functional silicone of formula (Si-3b)

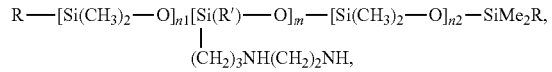

(Si-3b)

in which
R denotes —OH, an (optionally ethoxylated and/or propoxylated) (C$_1$ to C$_{20}$) alkoxy group or a —CH$_3$ group,
R' denotes —OH, a (C$_1$ to C$_{20}$) alkoxy group or a —CH$_3$ group and
m, n1 and n2 are numbers, the sum of which (m+n1+n2) amounts to between 1 and 2000, preferably between 50 and 150, wherein the sum of (n1+n2) preferably assumes values from 0 to 1999 and in particular from 49 to 149 and m preferably assumes values from 1 to 2000, in particular from 1 to 10.

According to the INCI declaration, these silicones are designated amodimethicones or functionalized amodimethicones, such as for example Bis(C13-15 Alkoxy) PG Amodimethicone (for example obtainable as the commercial product DC 8500 from Dow Corning), Trideceth-9 PG-Amodimethicone (for example obtainable as the commercial product Silcare Silicone SEA from Clariant).

Suitable diquaternary silicones are selected from compounds of general formula (Si3c)

(Si3c)

wherein the residues R$^1$ to R$^6$ mutually independently mean C$_1$ to C$_{22}$ alkyl residues which may include hydroxyl groups and wherein preferably at least one of the residues has at least 8 C atoms and the remaining residues have 1 to 4 C atoms,
residues R$^7$ to R$^{12}$ are mutually independently identical or different and mean C$_1$ to C$_{10}$ alkyl or phenyl, A means a divalent organic linking group,
n is a number from 0 to 200, preferably from 10 to 120, more preferably from 10 to 40, and X$^-$ is an anion.

The divalent linking group is preferably a C$_1$ to C$_{12}$ alkylene or alkoxyalkylene group which may be substituted with one or more hydroxyl groups.

The group —(CH$_2$)$_3$—O—CH$_2$—CH(OH)—CH$_2$— is more preferred.

The anion X$^-$ may be a halide ion, an acetate, an organic carboxylate or a compound of general formula RSO$_3^-$, in which R has the meaning of C$_1$ to C$_4$ alkyl residues.

A preferred diquaternary silicone has the general formula (Si3d)

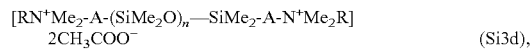

(Si3d), wherein A is the group —(CH$_2$)$_3$—O—CH$_2$—CH(OH)—CH$_2$—,
R is an alkyl residue with at least 8 C atoms and n a number from 10 to 120.

Suitable silicone polymers with two terminal quaternary ammonium groups are known by the INCI name Quaternium-80. These are dimethylsiloxanes with two terminal trialkylammonium groups. Such diquaternary polydimethylsiloxanes are distributed by Evonik under the trade names Abil® Quat 3270, 3272 and 3474.

Hair treatment agents which are preferred according to the invention are characterized in that, relative to the weight thereof, they include 0.01 to 10 wt. %, preferably 0.01 to 8 wt. %, more preferably 0.1 to 7.5 wt. % and in particular 0.2 to 5 wt. % of amino-functional silicone(s) and/or diquaternary silicone.

Further cationic aminosilicones with at least three terminal amino-functional groups have only recently been commercially offered for sale. These cationic silicone polymers are distinguished in that they have a silicone backbone and at least one polyether moiety and furthermore at least one moiety with an ammonium structure. Examples of the preferred cationic silicone polymers for the purposes of the present invention are in particular the compounds with the INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22 and Silicone Quaternium-2 Panthenol Succinate and Silicone Quaternium-16/Glycidyl Dimethicone Crosspolymer. Silicone Quaternium-22 is in particular most preferred. This raw material is distributed for example by Evonik under the trade name Abil® T-Quat 60.

The cationic aminofunctional silicone polymers are present in the compositions according to the invention in quantities of 0.01 to 5 wt. %, preferably in quantities of 0.05 to 5 wt. % and particularly preferably in quantities of 0.1 to 5 wt. %. The very best results are obtained with quantities of 0.1 to 2.5 wt. %, in each case relative to the total composition of the respective agent.

Polyammonium-polysiloxane compounds are further silicones according to the invention with amino functions. The polyammonium-polysiloxane compounds may for example be obtained from GE Bayer Silicones under the trade name Baysilone®. The products named Baysilone TP 3911, SME 253 and SFE 839 are here preferred. It is particularly preferred to use Baysilone TP 3911 as an active component of the compositions according to the invention. The polyammonium-polysiloxane compounds are used in the compositions according to the invention in a quantity of 0.01 to 10 wt. %, preferably 0.01 to 7.5, more preferably 0.01 to 5.0 wt. %, particularly preferably of 0.05 to 2.5 wt. % in each case relative to the total composition.

The cyclic dimethicones designated according to INCI as cyclomethicones may preferably be used according to the invention. Cosmetic or dermatological preparations which are preferred according to the invention are those which include at least one silicone of formula (Si-4)

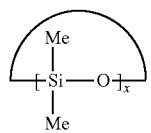

(Si-4)

in which x denotes a number from 3 to 200, preferably from 3 to 10, more preferably from 3 to 7 and in particular 3, 4, 5 or 6.

Agents which are likewise preferred according to the invention are those which are characterized in that they include at least one silicone of formula (Si-5)

$$R_3Si-[O-SiR_2]_x-(CH_2)_n-[O-SiR_2]_y-O-SiR_3 \quad (Si-5),$$

in which R denotes identical or different residues from the group —H, phenyl, benzyl, —CH$_2$—CH(CH$_3$)Ph, C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y denote a number from 0 to 200, preferably from 0 to 10, more preferably from 0 to 7 and in particular 0, 1, 2, 3, 4, 5 or 6, and n denotes a number from 0 to 10, preferably from 1 to 8 and in particular 2, 3, 4, 5, 6.

Further silicones which may be present in the compositions according to the invention, in addition to the dimethicones, dimethiconols, amodimethicones and/or cyclomethicones according to the invention, are water-soluble silicones.

Corresponding hydrophilic silicones are selected, for example, from the compounds of formulae (Si-6) and/or (Si-7). Particularly preferred water-soluble silicone-based surfactants are selected from the group of dimethicone copolyols which are preferably alkoxylated, in particular polyethoxylated or polypropoxylated.

According to the invention, dimethicone copolyols are preferably taken to mean polyoxyalkylene-modified dimethylpolysiloxanes of the general formulae (Si-6) or (Si-7):

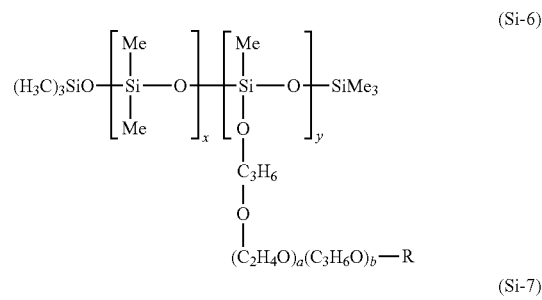

(Si-6)

(Si-7)

in which the residue R denotes a hydrogen atom, an alkyl group with 1 to 12 C atoms, an alkoxy group with 1 to 12 C atoms or a hydroxyl group, the residues R' and R" mean alkyl groups with 1 to 12 C atoms, x denotes an integer from 1 to 100, preferably from 20 to 30, y denotes an integer from 1 to 20, preferably from 2 to 10 and a and b denote integers from 0 to 50, preferably from 10 to 30.

Dimethicone copolyols which are more preferred for the purposes of the invention are for example the products commercially distributed under the trade name SILWET (Union Carbide Corporation) and DOW CORNING. Dimethicone copolyols which are more preferred according to the invention are Dow Corning 190 and Dow Corning 193.

The dimethicone copolyols are in the compositions according to the invention in quantities of 0.01 to 10 wt. %, preferably 0.01 to 8 wt. %, more preferably 0.1 to 7.5 wt. % and in particular 0.1 to 5 wt. % of dimethicone copolyol relative to the composition.

Ester oils may particularly preferentially be present as oil bodies in active substance combinations according to the invention. Ester oils are defined as follows:

Ester oils should be taken to mean the esters of C$_6$-C$_{30}$ fatty acids with C$_2$-C$_{30}$ fatty alcohols. The monoesters of fatty acids with alcohols with 2 to 24 C atoms are preferred. Examples of fatty acid moieties used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and the technical mixtures thereof. Examples of fatty alcohol moieties in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof. More preferred substances according to the invention are isopropyl myristate (Rilanit® IPM), isononanoic acid C$_{16-18}$ alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), Oleyl Oleate (Cetiol®), lauric acid hexyl ester (Cetiol® A), di-n-butyl adipate (Cetiol® B), myristyl myristate (Cetiol® mm), Cetearyl Isononanoate (Cetiol® SN), oleic acid decyl ester (Cetiol® V).

The ester oils may, of course, also be alkoxylated with ethylene oxide, propylene oxide or mixtures of ethylene oxide and propylene oxide. Alkoxylation may here proceed not only on the fatty alcohol moiety and the fatty acid moiety but also on both moieties of the ester oils. It is, however, preferred according to the invention if the fatty alcohol was alkoxylated first and then esterified with fatty acid. Formula (D4-II) is a general representation of these compounds.

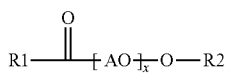

(D4-II)

$R^1$ here denotes a saturated or unsaturated, branched or unbranched, cyclic saturated or cyclic unsaturated acyl residue with 6 to 30 carbon atoms,
AO denotes ethylene oxide, propylene oxide or butylene oxide,
X denotes a number between 1 and 200, preferably 1 and 100, more preferably between 1 and 50, particularly preferably between 1 and 20, highly preferably between 1 and 10 and most preferably between 1 and 5,
$R^2$ denotes a saturated or unsaturated, branched or unbranched, cyclic saturated or cyclic unsaturated alkyl, alkenyl, alkynyl, phenyl or benzyl residue with 6 to 30 carbon atoms. Examples of fatty acid moieties used as residue $R^1$ in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and the technical mixtures thereof. Examples of fatty alcohol moieties as residue $R^2$ in the ester oils are benzyl alcohol, isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof. One ester oil which is more preferred according to the invention is for example obtainable under the INCI name PPG-3 Benzyl Ether Myristate.

Ester oils should furthermore be taken to be:
dicarboxylic acid esters such as di-n-butyl adipate, di-(2-ethylhexyl) adipate, di-(2-ethylhexyl) succinate and diisotridecyl acelate and diol esters such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate, and
symmetrical, asymmetrical or cyclic esters of carbonic acid with fatty alcohols, for example glycerol carbonate or dicaprylyl carbonate (Cetiol® CC),
trifatty acid esters of saturated and/or unsaturated linear and/or branched fatty acids with glycerol,
fatty acid partial glycerides, i.e. monoglycerides, diglycerides and the technical mixtures thereof. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and the technical mixtures thereof. Preferably, oleic acid monoglycerides are used.

The ester oils are used in the agents according to the invention in a quantity of 0.01 to 20 wt. %, preferably 0.01 to 10.0 wt. %, more preferably 0.01 to 7.5 wt. %, highly preferably of 0.1 to 5.0 wt. %. It is, of course, also possible according to the invention to use a plurality of ester oils simultaneously.

Further oil bodies according to the invention are:
plant oils. Examples of such oils are sunflower oil, olive oil, soy oil, rapeseed oil, almond oil, jojoba oil, orange oil, wheat germ oil, peach stone oil and the liquid fractions of coconut oil. However, other triglyceride oils such as the liquid fractions of beef fat together with synthetic triglyceride oils are also suitable.
liquid paraffin oils, isoparaffin oils and synthetic hydrocarbons and di-n-alkyl ethers with a total of between 12 and 36 C atoms, in particular 12 to 24 C atoms, such as for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and di-tert.-butyl ether, di-iso-pentyl ether, di-3-ethyldecyl ether, tert.-butyl-n-octyl ether, iso-pentyl-n-octyl ether and 2-methylpentyl-n-octyl ether. The compounds 1,3-di-(2-ethylhexyl)cyclohexane (Cetiol® S) and di-n-octyl ether (Cetiol®OE) obtainable as commercial products may be preferred.

Natural oils which are used are for example amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, cocoa butter, linseed oil, macadamia nut oil, maize germ oil, almond oil, marula oil, evening primrose oil, olive oil, palm oil, rapeseed oil, rice oil, sea buckthorn fruit oil, sea buckthorn seed oil, sesame oil, shea butter, soy oil, sunflower oil, grapeseed oil, walnut oil or wild rose oil.

It goes without saying that, in addition to the active substance combination according to the invention, the hair treatment agents according to the invention also include further components conventional in cosmetic compositions. The selection of these components is generally determined by the intended use of the hair treatment agents. In the case of a shampoo, further surface-active substances will, for example, be present. In the case of hair masks, further cationic compounds and further conditioning substances will optionally be present. In many cases, the agents include at least one surfactant, wherein not only anionic but also in principle zwitterionic, ampholytic, nonionic and cationic surfactants are suitable. The surface-active substances are selected on the basis of the nature of the agent.

Anionic surfactants (Tanion) which are suitable in preparations according to the invention are any anionic surface-active substances suitable for use on the human body. Typical examples of anionic surfactants are:
linear and branched fatty acids with 8 to 30 C atoms (soaps),
ether carboxylic acids of formula R—O—($CH_2$—$CH_2O)_x$—$CH_2$—COOH, in which R is a linear alkyl group with 8 to 30 C atoms and x=0 or 1 to 16 and the salts thereof,
acyl sarcosides with 8 to 24 C atoms in the acyl group,
acyl taurides with 8 to 24 C atoms in the acyl group,
acyl isethionates with 8 to 24 C atoms in the acyl group, sulfosuccinic acid mono- and diallyl esters with 8 to 24 C atoms in the alkyl group and sulfosuccinic acid monoalkyl polyoxyethyl esters with 8 to 24 C atoms in the alkyl group and 1 to 6 oxyethyl groups.

linear alkane sulfonates with 8 to 24 C atoms, linear alpha-olefin sulfonates with 8 to 24 C atoms, alpha-sulfofatty acid methyl esters of fatty acids with 8 to 30 C atoms, alkyl sulfates and alkyl polyglycol ether sulfates of formula R—O(CH$_2$—CH$_2$O)$_x$—OSO$_3$H, in which R is a preferably linear alkyl group with 8 to 30 C atoms and x=0 or 1 to 12, hydroxysulfonates substantially corresponding to at least one of the two following formulae or mixtures thereof and the salts thereof, CH$_3$—(CH$_2$)$_y$—CHOH—(CH$_2$)$_p$—(CH—SO$_3$M)-(CH$_2$)$_z$—CH$_2$—O—(C$_n$H$_{2n}$O)$_x$—H, and/or CH$_3$—(CH$_2$)$_y$—(CH—SO$_3$M)-(CH$_2$)$_p$—CHOH—(CH$_2$)$_z$—CH$_2$—O—(C$_n$H$_{2n}$O)$_x$—H wherein in both formulae y and z=0 or integers from 1 to 18, p=0, 1 or 2 and the sum (y+z+p) is a number from 12 to 18, x=0 or a number from 1 to 30 and n an integer from 2 to 4 and M=H or an alkali metal ion, in particular sodium, potassium or lithium, alkaline earth metal ion, in particular magnesium, calcium or zinc, and/or an ammonium ion, which may optionally be substituted, in particular mono-, di-, tri- or tetraammonium ions with C$_1$ to C$_4$ alkyl, alkenyl or aryl residues, sulfated hydroxyalkyl polyethylene glycol ethers and/or hydroxyalkylene propylene glycol ethers of formula R$^1$—(CHOSO$_3$M)-CHR$^3$—(OCHR$^4$—CH$_2$)$_n$—OR$^2$ where R$^1$ is a linear alkyl residue with 1 to 24 C atoms, R$^2$ denotes a linear or branched, saturated alkyl residue with 1 to 24 C atoms, R$^3$ denotes hydrogen or a linear alkyl residue with 1 to 24 C atoms, R$^4$ denotes hydrogen or a methyl residue and M denotes hydrogen, ammonium, alkylammonium, alkanolammonium, in which the alkyl and alkanol residues in each case have 1 to 4 C atoms, or a metal atom selected from lithium, sodium, potassium, calcium or magnesium and n denotes a number in the range from 0 to 12 and furthermore the total number of C atoms present in R$^1$ and R$^3$ amounts to 2 to 44, sulfonates of unsaturated fatty acids with 8 to 24 C atoms and 1 to 6 double bonds, esters of tartaric acid and citric acid with alcohols which are addition products of approximately 2-15 molecules of ethylene oxide and/or propylene oxide onto fatty alcohols with 8 to 22 C atoms, alkyl and/or alkenyl ether phosphates of formula, R$^1$(OCH$_2$CH$_2$)$_n$—O—(PO—OX)—OR$^2$, in which R$^1$ preferably denotes an aliphatic hydrocarbon residue with 8 to 30 carbon atoms, R$^2$ denotes hydrogen, a residue (CH$_2$CH$_2$O)$_n$R$^2$ or X, n denotes numbers from 1 to 10 and X denotes hydrogen, an alkali or alkaline earth metal or NR$^3$R$^4$R$^5$R$^6$, with R$^3$ to R$^6$ mutually independently denoting hydrogen or a C$_1$ to C$_4$ hydrocarbon residue, sulfated fatty acid alkylene glycol esters of formula RCO(AlkO)$_n$SO$_3$M in which RCO denotes a linear or branched, aliphatic, saturated and/or unsaturated acyl residue with 6 to 22 C atoms, Alk denotes CH$_2$CH$_2$, CHCH$_3$CH$_2$ and/or CH$_2$CHCH$_3$, n denotes numbers from 0.5 to 5 and M denotes a metal, such as an alkali metal, in particular sodium, potassium or lithium, an alkaline earth metal, in particular magnesium, calcium or zinc, or an ammonium ion, such as $^+$NR$^3$R$^4$R$^5$R$^6$, with R$^3$ to R$^6$ mutually independently denoting hydrogen or a C$_1$ to C$_4$ hydrocarbon residue, monoglyceride sulfates and monoglyceride ether sulfates of formula

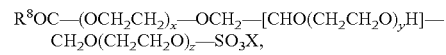

R$^8$OC—(OCH$_2$CH$_2$)$_x$—OCH$_2$—[CHO(CH$_2$CH$_2$O)$_y$H]—CH$_2$O(CH$_2$CH$_2$O)$_z$—SO$_3$X, in which R$^8$CO denotes a linear or branched acyl residue with 6 to 22 carbon atoms, x, y and z in total denote 0 or denote numbers from 1 to 30, preferably 2 to 10, and X denotes an alkali or alkaline earth metal. Typical examples of monoglyceride ether sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride and the ethylene oxide addition products thereof with sulfur trioxide or chlorosulfonic acid in the form of the sodium salts thereof. Preferably, monoglyceride sulfates are used, in which R$^8$CO denotes a linear acyl residue with 8 to 18 carbon atoms, amide-ether carboxylic acids R$^1$—CO—NR$^2$—CH$_2$CH$_2$—O—(CH$_2$CH$_2$O)$_n$CH$_2$COOM, where R$^1$ is a straight-chain or branched alkyl or alkenyl residue with a number of carbon atoms in the chain of 2 to 30, n denotes an integer from 1 to 20 and R$^2$ denotes hydrogen, a methyl, ethyl, propyl, isopropyl, n-butyl, t-butyl or iso-butyl residue and M denotes hydrogen or a metal such as an alkali metal, in particular sodium, potassium or lithium, an alkaline earth metal, in particular magnesium, calcium or zinc, or an ammonium ion, such as $^+$NR$^3$R$^4$R$^5$R$^6$, with R$^3$ to R$^6$ mutually independently denoting hydrogen or a C$_1$ to C$_4$ hydrocarbon residue. Such products are obtainable for example from Chem-Y under the product name Akypo®.

acyl glutamates of formula XOOC—CH$_2$CH$_2$CH(C(NH)OR)—COOX, in which RCO denotes a linear or branched acyl residue with 6 to 22 carbon atoms and 0 and/or 1, 2 or 3 double bonds and X denotes hydrogen, an alkali metal and/or alkaline earth metal, ammonium, alkylammonium, alkanolammonium or glucammonium, condensation products of a water-soluble salt of a water-soluble protein hydrolysate with a C$_8$-C$_{30}$ fatty acid. Such products have long been commercially obtainable under the trademarks Lamepon®, Maypon®, Gluadin®, Hostapon® KCG or Amisoft®.

alkyl and/or alkenyl oligoglycoside carboxylates, sulfates, phosphates and/or isethionates, acyl lactylates and hydroxy mixed ether sulfates.

If the mild anionic surfactants include polyglycol ether chains, it is particularly preferable for them to have a narrow homolog distribution. Furthermore, in the case of mild anionic surfactants with polyglycol ether units, it is preferred for the number of glycol ether groups to amount to 1 to 20, preferably 2 to 15, more preferably 2 to 12. Particularly mild anionic surfactants with polyglycol ether groups without a narrow homolog distribution may for example also be obtained if, on the one hand, the number of polyglycol ether groups amounts to 4 to 12 and Zn or Mg ions are selected as the counterion. One example of these is the commercial product Texapon® ASV.

Nonionic surfactants (Tnio) are for example addition products of 2 to 50 mol of ethylene oxide and/or 0 to 5 mol of propylene oxide onto linear and branched fatty alcohols with 6 to 30 C atoms, fatty alcohol polyglycol ethers or fatty alcohol polypropylene glycol ethers or mixed fatty alcohol polyethers, addition products of 2 to 50 mol of ethylene oxide and/or 0 to 5 mol of propylene oxide onto linear and branched fatty acids with 6 to 30 C atoms, fatty acid polyglycol ethers or fatty acid polypropylene glycol ethers or mixed fatty acid polyethers, addition products of 2 to 50 mol of ethylene oxide and/or 0 to 5 mol of propylene oxide onto linear and branched alkylphenols with 8 to 15 C atoms in the alkyl group, alkylphenol polyglycol ethers or alkyl polypropylene glycol ethers, or mixed alkylphenol polyethers, addition products, end group-terminated with a methyl or $C_2$-$C_6$ alkyl residue, of 2 to 50 mol of ethylene oxide and/or 0 to 5 mol of propylene oxide onto linear and branched fatty alcohols with 8 to 30 carbon atoms, onto fatty acids with 8 to 30 C atoms and onto alkylphenols with 8 to 15 C atoms in the alkyl group, such as for example the grades obtainable under the commercial names Dehydol® LS, Dehydol® LT (Cognis), $C_{12}$-$C_{30}$ fatty acid mono- and diesters of addition products of 1 to 30 mol of ethylene oxide onto glycerol, addition products of 5 to 60 mol ethylene oxide onto castor oil and hardened castor oil, polyol fatty acid esters, such as for example the commercial product Hydagen® HSP (Cognis) or Sovermol grades (Cognis), alkoxylated triglycerides, alkoxylated fatty acid alkyl esters of formula (Tnio-1)

 (Tnio-1)

in which $R^1CO$ denotes a linear or branched, saturated and/or unsaturated acyl residue with 6 to 22 carbon atoms, $R^2$ denotes hydrogen or methyl, $R^3$ denotes linear or branched alkyl residues with 1 to 4 carbon atoms and w denotes numbers from 1 to 20, amine oxides hydroxy mixed ethers, $R^1O[CH_2CH(CH_3)O]_x(CH_2CHR^2O)_y[CH_2CH(OH)R^3]_z$ with $R^1$ denoting a linear or branched, saturated or unsaturated alkyl and/or alkenyl residue with 2 to 30 C atoms, $R^2$ denoting hydrogen, a methyl, ethyl, propyl or iso-propyl residue, $R^3$ denoting a linear or branched alkyl residue with 2 to 30 C atoms, x denoting 0 or a number from 1 to 20, Y denoting a number from 1 to 30 and z denoting the number 1, 2, 3, 4 or 5.

sorbitan fatty acid esters and addition products of ethylene oxide onto sorbitan fatty acid esters such as for example polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type, sugar surfactants of the fatty acid N-alkyl polyhydroxyalkylamide type, fatty acid amide polyglycol ethers, fatty amine polyglycol ethers, mixed ethers or mixed formals and polysorbates.

Cationic surfactants of formula (Tkat1) may additionally be used.

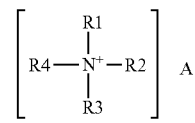 (Tkat1)

In the formula (Tkat1), $R^1$, $R^2$, $R^3$ and $R^4$ in each case mutually independently denote hydrogen, a methyl group, a phenyl group, a benzyl group, a saturated, branched or unbranched alkyl residue with a chain length of 8 to 30 carbon atoms, which may optionally be substituted with one or more hydroxyl groups. A denotes a physiologically acceptable anion, for example halides such as chloride or bromide and methosulfates.

Examples of compounds of formula (Tkat1) are laurylt-rimethylammonium chloride, cetyltrimethylammonium chloride, cetyltrimethylammonium bromide, cetyltrimethylammonium methosulfate, dicetyldimethylammonium chloride, tricetylmethylammonium chloride, stearyltrimethylammonium chloride, distearyldimethylammonium chloride, lauryldimethylbenzylammonium chloride, behenyltrimethylammonium chloride, behenyltrimethylammonium bromide, behenyltrimethylammonium methosulfate.

The surfactants (T) are used in quantities of 0.05-45 wt. %, preferably of 0.1-30 wt. % and particularly preferably of 0.5-25 wt. %, relative to the total agent used according to the invention.

Examples of emulsifiers which may be used according to the invention are:

addition products of 4 to 30 mol of ethylene oxide and/or 0 to 5 mol of propylene oxide onto linear fatty alcohols with 8 to 22 C atoms, onto fatty acids with 12 to 22 C atoms and onto alkylphenols with 8 to 15 C atoms in the alkyl group, $C_{12}$-$C_{22}$ fatty acid mono- and diesters of addition products of 1 to 30 mol of ethylene oxide onto polyols with 3 to 6 carbon atoms, in particular onto glycerol, ethylene oxide and polyglycerol addition products onto methyl glucoside/fatty acid esters, fatty acid alkanolamides and fatty acid glucamides, $C_8$-$C_{22}$ alkyl mono- and oligoglycosides and the ethoxylated analogs thereof, wherein degrees of oligomerization of 1.1 to 5, in particular of 1.2 to 2.0, and glucose as the sugar component are preferred, mixtures of alkyl(oligo)glucosides and fatty alcohols, for example the commercially obtainable product Montanov®68, addition products of 5 to 60 mol of ethylene oxide onto castor oil and hardened castor oil, partial esters of polyols with 3-6 carbon atoms with saturated fatty acids with 8 to 22 C atoms, sterols, both from animal tissue (zoosterols, cholesterol, lanosterol) and from plant fats (phytosterols, ergosterol, stigmasterol, sitosterol) or from fungi and yeasts (mycosterols), phospholipids (lecithins, phosphatidylcholines), fatty acid esters of sugars and sugar alcohols, such as sorbitol, polyglycerols and polyglycerol derivatives such as for example polyglycerol poly-12-hydroxystearate (commercial product Dehymuls® PGPH).

The agents according to the invention preferably include the emulsifiers in quantities of 0.1-25 wt. %, in particular of 0.5-15 wt. %, relative to the total agent.

The compositions according to the invention particularly preferably include fatty substances (Fat) as a further active substance. Fatty substances (Fat) should be taken to mean fatty acids, fatty alcohols, natural and synthetic waxes, which may assume both solid form and liquid form in an aqueous dispersion, and natural and synthetic cosmetic oil components.

Fatty acids (Fatac) which may be used are linear and/or branched, saturated and/or unsaturated fatty acids with 6-30 carbon atoms. Fatty acids with 10-22 carbon atoms are preferred. Such substances which may, for example, be mentioned are isostearic acid, such as the commercial products Emersol® 871 and Emersol® 875, and isopalmitic acids such as the commercial product Edenor® IP 95, and any further fatty acids distributed under the trade name Edenor® (Cognis). Further typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and the technical mixtures thereof. The fatty acid cuts obtainable from coconut oil or palm oil are conventionally more preferred; in general, it is more preferred to use stearic acid.

The quantity used here amounts to 0.1-15 wt. %, relative to the total agent. Preferably, the quantity amounts to 0.5-10 wt. %, wherein quantities of 1-5 wt. % are particularly advantageous.

Fatty alcohols (Fatal) which may be used are saturated, mono- or polyunsaturated, branched or unbranched fatty alcohols with $C_6$-$C_{30}$, preferably $C_{10}$-$C_{22}$ and particularly preferably $C_{12}$-$C_{22}$ carbon atoms. For the purposes of the invention, it is for example possible to use decanol, octanol, octenol, dodecenol, decenol, octadienol, dodecadienol, decadienol, oleyl alcohol, erucic alcohol, ricinol alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and the Guerbet alcohols thereof, wherein this list is intended to be of an exemplary and non-limiting nature. The fatty alcohols are, however, preferably derived from natural fatty acids, wherein the conventional starting point is isolation from the fatty acid esters by reduction. Fatty alcohol cuts which are a mixture of various fatty alcohols may likewise be used according to the invention. Such substances are commercially obtainable for example under the names Stenol®, for example Stenol® 1618 or Lanette®, for example Lanette® O or Lorol®, for example Lorol® C8, Lorol® C14, Lorol® C18, Lorol® C8-18, HD-Ocenol®, Crodacol®, for example Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Wool wax alcohols, as are for example commercially obtainable under the names Corona®, White Swan®, Coronet® or Fluilan®, may of course also be used according to the invention. The fatty alcohols are used in quantities of 0.1-30 wt. %, relative to the total preparation, preferably in quantities of 0.1-20 wt. %.

Natural or synthetic waxes (Fatwax) which may be used according to the invention are solid paraffins or isoparaffins, carnauba waxes, beeswaxes, candelilla waxes, ozokerites, ceresin, spermaceti, sunflower wax, fruit waxes such as for example apple wax or citrus wax, PE or PP microwaxes. Such waxes are obtainable for example through Kahl & Co., Trittau.

The quantity used amounts to 0.1-50 wt. % relative to the total agent, preferably 0.1-20 wt. % and more preferably 0.1-15 wt. % relative to the total agent.

The total quantity of oil and fat components in the agents according to the invention conventionally amounts to 0.5-75 wt. %, relative to the total agent. Quantities of 0.5-35 wt. % are preferred according to the invention.

A further preferred group of ingredients of the compositions according to the invention with the active substance complex according to the invention are vitamins, provitamins or vitamin precursors. Vitamins, provitamins and vitamin precursors which are more preferred are those which are assigned to groups A, B, C, E, F and H.

The group of substances designated vitamin A includes retinol (vitamin $A_1$) and 3,4-didehydroretinol (vitamin $A_2$). β-Carotene is the provitamin of retinol. Examples of substances which may be considered according the invention as the vitamin A component are vitamin A acid and the esters thereof, vitamin A aldehyde and vitamin A alcohol and the esters thereof such as the palmitate and the acetate. The agents according to the invention preferably include the vitamin A component in quantities of from 0.05-1 wt. %, relative to the total preparation.

The vitamin B group or the vitamin B complex includes, inter alia:
vitamin $B_1$ (thiamin)
vitamin $B_2$ (riboflavin)
vitamin $B_3$. This designation is frequently used for the compounds nicotinic acid and nicotinamide (niacinamide). Nicotinamide is preferred according to the invention and is preferably present in the agents according to the invention in quantities of from 0.05 to 1 wt. %, relative to the total agent.

Vitamin $B_5$ (pantothenic acid, panthenol and pantolactone). In the context of this group, panthenol and/or pantolactone are preferably used. Derivatives of panthenol which may be used according to the invention are in particular the esters and ethers of panthenol and cationically derivatized panthenols. Individual representatives are for example panthenol triacetate, panthenol monoethyl ether and the monoacetate thereof and cationic panthenol derivatives. Pantothenic acid is preferably used in the present invention as a derivative in the form of the more stable calcium salts and sodium salts (Ca pantothenate, Na pantothenate).

Vitamin $B_6$ (pyridoxine as well as pyridoxamine and pyridoxal).

The stated compounds of the vitamin B type, in particular vitamin $B_3$, $B_5$ and $B_6$, are preferably present in the agents according to the invention in quantities of from 0.05-10 wt. %, relative to the total agent. Quantities of 0.1-5 wt. % are more preferred.

Vitamin C (ascorbic acid). Vitamin C is preferably used in the agents according to the invention in quantities of from 0.1 to 3 wt. %, relative to the total agent. Use in the form of the palmitic acid ester, the glucosides or phosphates may be preferred. Use in combination with tocopherols may likewise be preferred.

Vitamin E (tocopherols, in particular α-tocopherol). Tocopherol and the derivatives thereof, which include in particular the esters such as the acetate, the nicotinate, the phosphate and the succinate, are preferably present in the agents according to the invention in quantities of from 0.05-1 wt. %, relative to the total agent.

Vitamin F. The term "vitamin F" is conventionally understood to mean essential fatty acids, in particular linoleic acid, linolenic acid and arachidonic acid.

Vitamin H. Vitamin H denotes the compound (3aS,4S, 6aR)-2-oxohexahydrothienol[3,4-d]-imidazole-4-valeric acid, which is now, however, known by the common name biotin. Biotin is present in the agents according to the invention preferably in quantities of from 0.0001 to 1.0 wt. %, in particular in quantities of from 0.001 to 0.01 wt. %.

The agents according to the invention preferably include vitamins, provitamins and vitamin precursors from the groups A, B, E and H. Panthenol, pantolactone, pyridoxine and the derivatives thereof and nicotinamide and biotin are more preferred.

In a further embodiment which is preferred according to the invention, the compositions according to the invention include bioquinones. In the agents according to the invention, suitable bioquinones should be taken to mean one or more ubiquinone(s) and/or plastoquinone(s). Ubiquinones which are preferred according to the invention have the following formula:

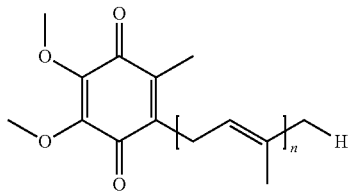

with $n = 6, 7, 8, 9$ or $10$.

Coenzyme Q-10 is here most preferred.

Preferred compositions according to the invention include purine and/or purine derivatives in relatively narrow quantity ranges. Cosmetic agents which are preferred according to the invention are here characterized in that, relative to the weight thereof, they include 0.001 to 2.5 wt. %, preferably 0.0025 to 1 wt. %, more preferably 0.005 to 0.5 wt. % and in particular 0.01 to 0.1 wt. % of purine(s) and/or purine derivative(s). Cosmetic agents which are preferred according to the invention are characterized in that they include purine, adenine, guanine, uric acid, hypoxanthine, 6-purinethiol, 6-thioguanine, xanthine, caffeine, theobromine or theophylline. Caffeine is most preferred in hair cosmetic preparations.

In a further preferred embodiment of the present invention, the cosmetic agent includes ectoine ((5)-2-methyl-1,4,5,6-tetrahydro-4-pyrimidinecarboxylic acid).

Agents which are more preferred according to the invention are those which, relative to the weight thereof, include 0.00001 to 10.0 wt. %, preferably 0.0001 to 5.0 wt. % and in particular 0.001 to 3 wt. % of the active substances from the group which is formed by carnitine, coenzyme Q-10, ectoine, a vitamin of the B series, a purine and the derivatives thereof or physiologically acceptable salts.

The action of the compositions according to the invention may furthermore be increased by a 2-pyrrolidinone-5-carboxylic acid and the derivatives thereof (J). The sodium, potassium, calcium, magnesium or ammonium salts, in which, in addition to hydrogen, the ammonium ion bears one to three $C_1$ to $C_4$ alkyl groups, are preferred. The sodium salt is particularly preferred. The quantities used in the agents according to the invention amount to 0.05 to 10 wt. %, relative to the total agent, more preferably 0.1 to 5, and in particular 0.1 to 3 wt. %.

Thanks to the use of plant extracts as conditioning substances, the hair treatment agents according to the invention may have a formulation which is particularly close to nature while nevertheless being very effective in terms of their conditioning performance. It is optionally even possible to dispense with the preservatives which would otherwise be conventional. According to the invention, preference is above all given to extracts from green tea, oak bark, stinging nettle, witch hazel, hops, henna, chamomile, burdock root, horsetail, hawthorn, lime blossom, almond, aloe vera, pine needle, horse chestnut, sandalwood, juniper, coconut, mango, apricot, lime, wheat, kiwi fruit, melon, orange, grapefruit, sage, rosemary, birch, mallow, valerian, lady's smock, wild thyme, yarrow, thyme, melissa, restharrow, coltsfoot, marsh mallow, meristem, ginseng, coffee, cocoa, moringa, ginger root and ayurvedic plant extracts, such as for example *Aegle marmelos* (bilwa), *Cyperus rotundus* (nagar motha), *Emblica officinalis* (amalaki), *Morida citrifolia* (ashyuka), *Tinospora cordifolia* (guduchi), *Santalum album* (chandana), *Crocus sativus* (kumkuma), *Cinnamonum zeylanicum* and *Nelumbo nucifera* (kamala), sweet grasses such as wheat, barley, rye, oats, spelt, maize, the various varieties of millet (proso millet, African finger millet, foxtail millet as examples), sugar cane, ryegrass, meadow foxtail, oat grass, bentgrass, meadow fescue, moor grass, bamboo, cotton grass, fountain grasses, Andropogoneae (*Imperata cylindrica* also known as blady grass or cogon grass), buffalo grass, cordgrasses, dog's tooth grasses, lovegrasses, Cymbopogon (lemon grass), Oryzeae (rice), Zizania (wild rice), marram grass, steppe oat, softgrasses, quaking grasses, bluegrasses, couch grasses and *Echinacea*, in particular *Echinacea purpurea* (L.) Moench, all species of vine and pericarp of *Litchi chinensis*.

The plant extracts may be used according to the invention in both pure and dilute form. Where used in dilute form, they conventionally include approximately 2-80 wt. % of active substance and, as solvent, the extracting agent or extracting agent mixture used to isolate them.

It may occasionally be necessary to use anionic polymers. Examples of anionic monomers of which such polymers may consist are acrylic acid, methacrylic acid, crotonic acid, maleic anhydride and 2-acrylamido-2-methylpropanesulfonic acid. In this case, the acidic groups may be present wholly or in part as a sodium, potassium, ammonium, mono- or triethanolammonium salt. 2-Acrylamido-2-methylpropanesulfonic acid and acrylic acid are preferred monomers.

Anionic polymers which have proven very particularly effective are those which include as sole or co-monomer 2-acrylamido-2-methylpropanesulfonic acid, wherein the sulfonic acid group may be present wholly or in part as a sodium, potassium, ammonium, mono- or triethanolammonium salt.

The homopolymer of 2-acrylamido-2-methylpropanesulfonic acid is more preferred, and is commercially obtainable for example under the name Rheothik® 11-80.

Preferred nonionogenic monomers are acrylamide, methacrylamide, acrylic acid esters, methacrylic acid esters, vinylpyrrolidone, vinyl ethers and vinyl esters.

Preferred anionic copolymers are acrylic acid-acrylamide copolymers and in particular polyacrylamide copolymers with monomers including sulfonic acid groups. Such a polymer is present in the commercial product Sepigel®305 from SEPPIC.

Anionic homopolymers which are likewise preferred are uncrosslinked and crosslinked polyacrylic acids. In this case, allyl ethers of pentaerythritol, of sucrose and of propylene may be preferred crosslinking agents. Such compounds are commercially obtainable for example under the trademark Carbopol®.

Copolymers of maleic anhydride and methyl vinyl ether, in particular those comprising crosslinks, are also colorpreserving polymers. A maleic acid-methyl vinyl ether copolymer crosslinked with 1,9-decadiene is commercially obtainable under the name Stabileze® QM.

The anionic polymers are present in the agents according to the invention preferably in quantities of from 0.05 to 10 wt. %, relative to the total agent. Quantities of 0.1 to 5 wt. % are more preferred.

In a further embodiment, the agents according to the invention may include nonionogenic polymers.

Suitable nonionogenic polymers are for example:
vinylpyrrolidone/vinyl ester copolymers, as are distributed for example under the tradename Luviskol® (BASF). Luviskol® VA 64 and Luviskol® VA 73, in each case vinylpyrrolidone/vinyl acetate copolymers, are likewise preferred nonionic polymers.
cellulose ethers, such as hydroxypropylcellulose, hydroxyethylcellulose and methylhydroxypropylcellulose, as are distributed for example under the tradenames Culminal® and Benece® (AQUALON) and Natrosol® grades (Hercules).
starch and the derivatives thereof, in particular starch ethers, for example Structure® XL (National Starch), a multifunctional, salt-tolerant starch;
shellac
polyvinylpyrrolidones, as are distributed for example under the tradename Luviskol® (BASF).

The nonionic polymers are present in the compositions according to the invention preferably in quantities of from 0.05 to 10 wt. %, relative to the total agent. Quantities of 0.1 to 5 wt. % are more preferred.

In a further embodiment, the agents according to the invention should additionally include at least one UV light protection filter. UVB filters may be oil-soluble or water-soluble.

Oil-soluble substances which may be mentioned are, for example:
3-benzylidene camphor, for example 3-(4-methylbenzylidene)camphor;
4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester;
esters of cinnamic acid, preferably 4-methoxycinnamic acid 2-ethylhexyl ester, 4-methoxycinnamic acid propyl ester, 4-methoxycinnamic acid isoamyl ester, 2-cyano-3-phenylcinnamic acid 2-ethylhexyl ester (octocrylene);
esters of salicylic acid, preferably salicylic acid 2-ethylhexyl ester, salicylic acid 4-isopropylbenzyl ester, salicylic acid homomenthyl ester;
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic acid, preferably 4-methoxybenzalmalonic acid di-2-ethylhexyl ester;
triazine derivatives, such as for example 2,4,6-trianilino-(p-carbo-2'-ethyl-1'-hexyloxy)-1,3,5-triazine and octyl triazone.
propane-1,3-diones, such as for example 1-(4-tert.-butylphenyl)-3-(4'-methoxyphenyl)propane-1,3-dione;

Water-soluble substances which may be considered are:
2-phenylbenzimidazole 5-sulfonic acid and the alkali and alkaline earth metal, ammonium, alkylammonium, alkanolammonium and glucammonium salts thereof;
sulfonic acid derivatives of benzophenones, preferably 2-hydroxy-4-methoxybenzophenone 5-sulfonic acid and the salts thereof;
sulfonic acid derivatives of 3-benzylidenecamphor, such as for example 4-(2-oxo-3-bornylidenemethyl)benzenesulfonic acid and 2-methyl-5-(2-oxo-3-bornylidene) sulfonic acid and the salts thereof Typical UVA filters which may be considered are in particular derivatives of benzoylmethane, such as for example 1-(4'-tert.-butylphenyl)-3-(4'-methoxyphenyl)propane-1,3-dione or 1-phenyl-3-(4'-isopropylphenyl)propane-1,3-dione. The UVA and UVB filters may, of course, also be used in mixtures. In addition to the stated soluble substances, insoluble pigments may also be considered for this purpose, in particular finely dispersed metal oxides or salts, such as for example titanium dioxide, zinc oxide, iron oxide, aluminum oxide, cerium oxide, zirconium oxide, silicates (talcum), barium sulfate and zinc stearate. The particles should here have an average diameter of less than 100 nm, preferably between 5 and 50 nm and in particular between 15 and 30 nm. They may have a spherical shape, but such particles having a shape which is ellipsoidal or differs in another way from spherical may also be used.

The cosmetic agents may moreover include further active substances, auxiliary substances and additives, such as for example
structuring agents such as maleic acid and lactic acid,
swelling agents such as urea, allantoin, carbonates or hydantoin,
dimethyl isosorbide and cyclodextrins,
dyes for coloring the agent,
antidandruff active substances such as piroctone olamine, zinc omadine and climbazole,
complexing agents such as EDTA, NTA, β-alaninediacetic acid and phosphonic acids,
opacifiers such as latex, styrene/PVP and styrene/acrylamide copolymers
pearlescent agents such as ethylene glycol mono- and distearate as well as PEG-3 distearate,
pigments,
stabilizers for hydrogen peroxide and other oxidizing agents,
propellants such as propane/butane mixtures, $N_2O$, dimethyl ether, $CO_2$ and air,
antioxidants,
perfume oils, scents and odorants.

With regard to further optional components and the quantities of these components used, reference is explicitly made to the relevant handbooks known to a person skilled in the art.

The invention therefore further provides a method for hair treatment, in which the hair treatment agent according to claim 1 is applied onto the hair and, after a period of exposure, rinsed out of the hair.

The period of exposure preferably amounts to a few seconds to 100 minutes, more preferably to 1 to 50 minutes and particularly preferably to 1 to 30 minutes.

A method in which the cosmetic agent according to claim 1 is applied onto the hair and remains there is furthermore according to the invention. According to the invention, "remain on the hair" is taken to mean that the agent is not rinsed back out of the hair immediately after the use of thereof. Instead, the agent remains on the hair in this case for more than 100 minutes up to until the next time the hair is washed.

Finally, use of a composition as previously described for reducing and/or delaying scalp desquamation is according to the invention.

The following examples are intended to explain the subject matter of the present invention but without limiting it.

EXAMPLES

Unless otherwise stated, all quantities are stated in parts by weight. The following formulations were prepared using known production methods.

Conditioning spray, also usable in mousse form and/or as a hair mask—the pH value of all formulations was adjusted to 2 to 6.

|  | K1 | K2 | K3 | K4 | K5 | K6 | K7 | K8 | K9 | K10 | K11 |
|---|---|---|---|---|---|---|---|---|---|---|---|
| Polymer JR 400 | 0.2 | 0.2 | 0.2 | 0.2 | 0.2 | 0.2 | 0.2 | 0.2 | 0.2 | 0.2 | 0.2 |
| Armocare VGH 70 | 0.5 | 0.5 | 0.5 | 0.5 | 0.5 | 0.5 | 0.5 | 0.5 | 0.5 | 0.5 | 0.5 |
| Stearamidopropyl Dimethylamine | 0.5 | 0.5 | 0.5 | 0.5 | 0.5 | 0.5 | 0.5 | 0.5 | 0.5 | 0.5 | 0.5 |
| PVP/VA copolymer 60/40 | 1.0 | 1.0 | 1.0 | 1.0 | 1.0 | 1.0 | 1.0 | 1.0 | 1.0 | 1.0 | 1.0 |
| CDHP* | 1.0 | 1.0 | 1.0 | 1.0 | 1.0 | 1.0 | 1.0 | 1.0 | 1.0 | 1.0 | — |
| Arginine | 0.1 | — | — | — | 0.1 | — | — | 0.1 | — | — | — |
| Glutamine | — | 0.1 | — | — | — | 0.1 | — | — | — | — | — |
| Carnitine | — | — | 0.1 | — | — | — | 0.1 | 0.1 | — | — | 0.1 |
| Taurine | — | — | — | 0.1 | 0.1 | 0.1 | 0.1 | 0.1 | — | 0.1 | — |
| Histidine | — | — | — | — | — | — | — | — | 0.1 | — | 0.1 |
| Lysine | — | — | — | — | — | — | — | — | — | 0.1 | — |
| Panthenol | 0.2 | 0.2 | 0.2 | 0.2 | 0.2 | 0.2 | 0.2 | 0.2 | 0.2 | 0.2 | 0.2 |
| Cetrimonium Chloride | 5.0 | 5.0 | 5.0 | 5.0 | 5.0 | 5.0 | 5.0 | 5.0 | 5.0 | 5.0 | 5.0 |
| Ceteareth-25 | 0.3 | 0.3 | 0.3 | 0.3 | 0.3 | 0.3 | 0.3 | 0.3 | 0.3 | 0.3 | 0.3 |
| ProSina | 0.2 | 0.2 | 0.2 | 0.2 | 0.2 | 0.2 | 0.2 | 0.2 | 0.2 | 0.2 | 0.2 |
| Dow Corning 193 | 0.2 | 0.2 | 0.2 | 0.2 | 0.2 | 0.2 | 0.2 | 0.2 | 0.2 | 0.2 | 0.2 |
| Silicone Quaternium-22 | 0.5 | 0.5 | 0.5 | 0.5 | 0.5 | 0.5 | 0.5 | 0.5 | 0.5 | 0.5 | 0.5 |
| Coco Betaine | 0.5 | 0.5 | 0.5 | 0.5 | 0.5 | 0.5 | 0.5 | 0.5 | 0.5 | 0.5 | 0.5 |
| Water, preservative and optionally perfume oils | ad 100 | ad 100 | ad 100 | ad 100 | ad 100 | ad 100 | ad 100 | ad 100 | ad 100 | ad 100 | ad 100 |

*Cetearamidoethyl Diethonium Hydrolyzed Protein

For application as a mousse, the formulation in question is either packaged with a propellant gas in an aerosol container or dispensed from a pump bottle with an appropriate pump attachment, such as for example Airfoamer, as a mousse. For use as a hair mask or cream, fatty alcohol such as cetylstearyl alcohol and/or ethylene glycol distearate and/or glycerol monostearate are added in quantities of 0.2 to 5.0 wt. % to the above stated formulations.

Shampoo:

|  | S1 | S2 | S3 | S4 | S5 | S6 | S7 | S8 | S9 | S10 | S11 |
|---|---|---|---|---|---|---|---|---|---|---|---|
| Texapon ® N70 | 15.0 | 15.0 | 15.0 | 15.0 | 15.0 | 15.0 | 15.0 | 15.0 | 15.0 | 15.0 | 15.0 |
| Arlypon ® F | 0.15 | 0.15 | 0.15 | 0.15 | 0.15 | 0.15 | 0.15 | 0.15 | 0.15 | 0.15 | 0.15 |
| Antil ® 141 | 0.15 | 0.15 | 0.15 | 0.15 | 0.15 | 0.15 | 0.15 | 0.15 | 0.15 | 0.15 | 0.15 |
| Disodium Cocoamphodiacetate | 6.0 | 6.0 | 6.0 | 6.0 | 6.0 | 6.0 | 6.0 | 6.0 | 6.0 | 6.0 | 6.0 |
| Polyquaternium-10 | 0.5 | 0.5 | 0.5 | 0.5 | 0.5 | 0.5 | 0.5 | 0.5 | 0.5 | 0.5 | 0.5 |
| CDHP* | 1.0 | 1.0 | 1.0 | 1.0 | 1.0 | 1.0 | 1.0 | 1.0 | 1.0 | 1.0 | 1.0 |
| Arginine | 0.1 | — | — | — | 0.1 | — | — | 0.1 | — | — | — |
| Glutamine | — | 0.1 | — | — | — | 0.1 | — | — | — | — | — |
| Carnitine | — | — | 0.1 | — | — | — | 0.1 | 0.1 | — | — | 0.1 |
| Taurine | — | — | — | 0.1 | 0.1 | 0.1 | 0.1 | 0.1 | — | 0.1 | — |
| Histidine | — | — | — | — | — | — | — | — | 0.1 | — | 0.1 |
| Lysine | — | — | — | — | — | — | — | — | — | 0.1 | — |
| Cetiol ® HE | 3.0 | 3.0 | 3.0 | 3.0 | 3.0 | 3.0 | 3.0 | 3.0 | 3.0 | 3.0 | 3.0 |
| Panthenol | 0.2 | 0.2 | 0.2 | 0.2 | 0.2 | 0.2 | 0.2 | 0.2 | 0.2 | 0.2 | 0.2 |
| Dow Corning ® 193 | 0.1 | 0.1 | 0.1 | 0.1 | 0.1 | 0.1 | 0.1 | 0.1 | 0.1 | 0.1 | 0.1 |
| Silicone Quaternium-22 | 1.0 | 1.0 | 1.0 | 1.0 | 1.0 | 1.0 | 1.0 | 1.0 | 1.0 | 1.0 | 1.0 |
| ProSina | 0.5 | 0.5 | 0.5 | 0.5 | 0.5 | 0.5 | 0.5 | 0.5 | 0.5 | 0.5 | 0.5 |
| Cremophor ® HRE 60 | 0.5 | 0.5 | 0.5 | 0.5 | 0.5 | 0.5 | 0.5 | 0.5 | 0.5 | 0.5 | 0.5 |

-continued

|  | S1 | S2 | S3 | S4 | S5 | S6 | S7 | S8 | S9 | S10 | S11 |
|---|---|---|---|---|---|---|---|---|---|---|---|
| Water, preservative and optionally perfume oils | ad 100 | ad 100 | ad 100 | ad 100 | ad 100 | ad 100 | ad 100 | ad 100 | ad 100 | ad 100 | ad 100 |

*Cetearamidoethyl Diethonium Hydrolyzed Protein

The pH value of all formulations was adjusted to 4.5 to 5.8.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition including in a suitable cosmetic carrier, in each case relative to the total weight of the composition,
    a) at least one protein hydrolysate in a total quantity of 0.01 to 10.0 wt. %,
    b) at least one selected complex of an acidic protein hydrolysate and a basic fatty acid amidoamine in a total quantity of 1.0 to 10.0 wt. %, the acid protein hydrolysate being selected from the group consisting of plant based protein hydrolysates, collagen hydrolysates, keratin hydrolysates, silk hydrolysates, and milk protein hydrolysates, and the basic fatty acid amidoamine having the structure $R^1—NR^2—(CH_2)^n—NR^3R^4R^5$,
    in which $R^1$ denotes a linear or branched, saturated or unsaturated acyl residue with 8 to 40 C atoms in the chain, $R^2$ denotes a $C_1$ to $C_4$ alkyl residue or hydrogen, $R^3$, $R^4$ and $R^5$ mutually independently denote hydrogen a methyl residue or a $C_2$ to $C_4$ alkyl residue, n denotes an integer selected from 1, 2, 3, 4 or 5, and
    c) 0.1 to 10.0 wt. % esterquats.

2. The cosmetic composition according to claim 1, wherein the selected complex of an acidic protein hydrolysate and a basic fatty acid amidoamine is selected from the group consisting of cetearamidoethyl diethonium hydrolyzed proteins.

3. The cosmetic composition according to claim 1, wherein the at least one selected complex of an acidic protein hydrolysate and a basic fatty acid amidoamine is cetearamidoethyl diethonium hydrolyzed wheat.

4. The cosmetic composition according to claim 1, wherein behentrimonium chloride and/or cetyltrimethylammonium chloride is/are used as a further cationic surfactant.

5. The cosmetic composition according to claim 1, further comprising at least one zwitterionic and/or amphoteric surfactant.

6. The cosmetic composition according to claim 5, wherein the zwitterionic and/or amphoteric surfactant is selected from the group consisting of cocamidopropyl betaine and coco betaine.

7. The cosmetic composition according to claim 1, further including at least one active substance selected from the group consisting of coenzyme Q-10, ectoine, a purine and derivatives and physiologically acceptable salts thereof, and a vitamin of the B series.

8. A method for treating keratinic fibers, including applying the cosmetic composition according to claim 1 onto the keratinic fibers and, after a period of exposure of a few seconds up to 45 minutes, rinsing the cosmetic composition back out.

* * * * *